United States Patent
Betancourt et al.

(10) Patent No.: US 11,946,072 B2
(45) Date of Patent: Apr. 2, 2024

(54) MEDIUM, METHODS, CELLS AND SECRETED FACTORS FOR STEM CELL CULTURE AND THERAPY

(71) Applicant: SanBio, Inc., Mountain View, CA (US)

(72) Inventors: Aline M. Betancourt, La Jolla, CA (US); Ruth S. Waterman, La Jolla, CA (US); Thomas F. Isett, Sparks, MD (US)

(73) Assignee: SanBio, Inc., Oakland, CA (US)

( * ) Notice: Subject to any disclaimer, the term of this patent is extended or adjusted under 35 U.S.C. 154(b) by 561 days.

(21) Appl. No.: 16/147,229

(22) Filed: Sep. 28, 2018

(65) Prior Publication Data
US 2019/0062710 A1    Feb. 28, 2019

Related U.S. Application Data

(63) Continuation of application No. PCT/US2017/025153, filed on Mar. 30, 2017.

(60) Provisional application No. 62/316,131, filed on Mar. 31, 2016.

(51) Int. Cl.
| | | |
|---|---|---|
| *C12N 5/0775* | (2010.01) | |
| *A61K 35/12* | (2015.01) | |
| *A61K 35/28* | (2015.01) | |
| *C07K 14/47* | (2006.01) | |
| *A61K 38/00* | (2006.01) | |

(52) U.S. Cl.
CPC ............ *C12N 5/0662* (2013.01); *A61K 35/12* (2013.01); *A61K 35/28* (2013.01); *C07K 14/4716* (2013.01); *C12N 5/0663* (2013.01); *A61K 38/00* (2013.01); *C12N 2500/02* (2013.01); *C12N 2501/30* (2013.01); *C12N 2501/998* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 11,046,929 B2 * | 6/2021 | Betancourt | A61P 25/02 |
| 11,311,650 B2 * | 4/2022 | Dashti | A61L 27/18 |
| 2010/0008992 A1 | 1/2010 | Ichim | |
| 2014/0017787 A1 * | 1/2014 | Betancourt | C12N 5/0667 |
| | | | 435/375 |
| 2014/0220053 A1 | 8/2014 | Muraca et al. | |
| 2014/0256043 A1 * | 9/2014 | Kume | A61K 31/475 |
| | | | 435/377 |
| 2015/0010517 A1 | 1/2015 | Chapman | |
| 2019/0353643 A1 * | 11/2019 | Yoo | C12N 5/0663 |
| 2021/0062140 A1 * | 3/2021 | Betancourt | A61P 29/00 |

FOREIGN PATENT DOCUMENTS

| | | | |
|---|---|---|---|
| CN | 104845933 | 8/2015 | |
| JP | 2012-031127 | 2/2012 | |
| JP | 2015-171389 | 10/2015 | |
| JP | 2015-532596 | 11/2015 | |
| KR | 10-2007-0073780 | 7/2007 | |
| KR | 2010-0014504 | 2/2010 | |
| KR | 10-1415039 | 8/2014 | |
| WO | WO-2012051210 A2 * | 4/2012 | ........... C12N 5/0667 |
| WO | WO 2017/173150 | 10/2017 | |

OTHER PUBLICATIONS

Wang, Y., Lu, X., He, J et al. Influence of erythropoietin on microvesicles derived from mesenchymal stem cells protecting renal function of chronic kidney disease. Stem Cell Res Ther 6, 100 (2015) (Year: 2015).*
Nazmul Haque, Mohammad Tariqur Rahman, Noor Hayaty Abu Kasim, Aied Mohammed Alabsi, "Hypoxic Culture Conditions as a Solution for Mesenchymal Stem Cell Based Regenerative Therapy", The Scientific World Journal, vol. 2013, Article ID 632972, 12 pages, 2013. (Year: 2013).*
Mimeault M, Batra SK. Recent progress on tissue-resident adult stem cell biology and their therapeutic implications. Stem Cell Rev. 2008;4(1):27-49. (Year: 2008).*
Qi C, Yan X, Huang C, Melerzanov A, Du Y. Biomaterials as carrier, barrier and reactor for cell-based regenerative medicine. Protein Cell. Sep. 2015;6(9):638-53. (Year: 2015).*
De Becker A, Riet IV. Homing and migration of mesenchymal stromal cells: How to improve the efficacy of cell therapy ?. World J Stem Cells. Mar. 2, 20166;8(3):73-87. (Year: 2016).*
Zhang J, Chopp M. Cell-based therapy for ischemic stroke. Expert Opinion on Biological Therapy. Sep. 1, 2013;13(9):1229-40. (Year: 2013).*
Garg R, Chaudhuri A, Munschauer F, Dandona P. Hyperglycemia, insulin, and acute ischemic stroke: a mechanistic justification for a trial of insulin infusion therapy. Stroke. Jan. 1, 2006;37(1):267-73. (Year: 2006).*
Waterman RS, Tomchuck SL, Henkle SL, Betancourt AM. A new mesenchymal stem cell (MSC) paradigm: polarization into a pro-inflammatory MSC1 or an Immunosuppressive MSC2 phenotype. PLoS one. Apr. 26, 2010;5(4):e10088; cited in IDS filed on Mar. 17, 2021. (Year: 2010).*
Mora-Lee S, Sirerol-Piquer MS, Gutiérrez-Pérez M, Gomez-Pinedo U, Roobrouck VD, Lopez T, Casado-Nieto M, Abizanda G, Rabena MT, Verfaille C, Prosper F. Therapeutic effects of hMAPC and hMSC transplantation after stroke in mice. PLoS One. 2012; 7(8):e43683. Epub Aug. 31, 2012. (Year: 2012).*
Yu SP, Wei Z, Wei L. Preconditioning strategy in stem cell transplantation therapy. Translational stroke research. Feb. 2013;4(1):76-88. (Year: 2013).*

(Continued)

Primary Examiner — Christopher M Babic
Assistant Examiner — E. Y. Pyla
(74) Attorney, Agent, or Firm — Levine Bagade Han LLP

(57) ABSTRACT

Described herein are methods and culture medium, useful for inducing polarization in multipotent stem cells. Additionally, described herein are multipotent cells produced by the methods and culture medium of this disclosure that are useful therapeutic agents. Also described herein are extracellular vesicles and factors secreted by multipotent cells that are produced by the methods and culture medium of this disclosure that are useful as therapeutic agents.

16 Claims, 5 Drawing Sheets

(56) References Cited

OTHER PUBLICATIONS

Bunnell BA, Betancourt AM, Sullivan DE. New concepts on the immune modulation mediated by mesenchymal stem cells. Stem Cell Res Ther. Nov. 11, 2010;1(5):34 (Year: 2010).*
Glenn JD, Whartenby KA. Mesenchymal stem cells: emerging mechanisms of immunomodulation and therapy. World journal of stem cells. Nov. 11, 2014;6(5):526. (Year: 2014).*
Tomchuck SL, Zwezdaryk KJ, Coffelt SB, Waterman RS, Danka ES, Scandurro AB. Toll-like receptors on human mesenchymal stem cells drive their migration and immunomodulating responses. Stem cells. Jan. 2008;26(1):99-107. (Year: 2008).*
Azarpira et al., Int J Stem Cell Res Ther 2015, 2:010, vol. 2, Issue 2, 5 pages (Year: 2015).*
Shekari et al., Am J of Clin Oncol, vol. 35, No. 6, Dec. 2012, pp. 514-519 (Year: 2012).*
Prabakar et al., Cell Transplantation, vol. 21, pp. 1321-1339, 2012 (Year: 2012).*
Li et al., Cell Death and Differentiation (2012) 19, 1505-1513 (Year: 2012).*
Li et al., Cell Death and Differentiation (2012) 19, 1505-1513, Supplementary Figure S9 (Year: 2012).*
Amariglio N. et al. "Donor-derived brain tumor following neural stem cell transplantation in an ataxia telangiectasia patient", PLoS Med. 2009; 6(2):e 100002; p. 1-3.
Fang, Xiaohui et al., "Human Mesenchymal 1-9 Stem (Stromal) Cells Promote the Resolution of Acute Lung Injury in Part through Lipoxin A 4," The Journal of Immunology, vol. 195, No. 3, pp. 875-881, Aug. 1, 2015.
Forterre A. et al. "Proteomic Analysis of C2C12 Myoblast and Myotube Exosome-Lilce Vesicles: A New Paradigm for Myoblast-Myotube Cross Talk?", PLOS ONE 9(I): 10.1371/annotation/ecdle074-2618-4ad0-95c0-efdb467c714b; DOI: 10.1371/journal.pone.0084153.
Gezsi, A., et al. "Systems biology approaches to investigating the roles of extracellular vesicles in human diseases", Experimental & Molecular Medicinevolume, 51:33, 2019; DOI: 10.1038/s12276-019-0226-2.
Huynh, A.S., et al. "Novel Toll-like Receptor 2 Ligands for Targeted Pancreatic Cancer Imaging and Immunotherapy", J Med Chem., 55(22):9751-9762, 2012; DOI: 10.1021/jm301002f.
Konoshenko, M.Y., et al. "Isolation of Extracellular Vesicles: General Methodologies and Latest Trends", Biomed Res Int., 2018: 8545347; DOI: 10.1155/2018/8545347.
Menzorov A.G. et al., "Why Collections of Cell Lines are Needed," Vavilovskiy zhurnal genetiki i selektsii [Vavilov Journal of Genetics and Selection]. 2016; 20(6):945-948; p. 947.
Menzorov A.G., "Mouse and human embryonic stem cells", Vavilovskiy zhurnal genetiki i selektsii [Vavilov Journal of Genetics and Selection]. 2013; 17(2): 234-245.
Panteleev M.A. et al. "Fisiologiya i patologiya vnekletochnyh vezikul" [Physiology and pathology of extracellular vesicles], Oncohematology. 2017; 1(12):62-70; DOI: 10.17650/1818-8346-2017-12-1-62-70.
Peri, F., et al. "Toll-like Receptor 4 (TLR4) modulation by synthetic and natural compounds: an update", J Med Chem., 57(9):3612-3622, 2014; DOI:10.1021/jm401006s.
Ranganath, Sudhir?h et al., "Harnessing 10-14 the Mesenchymal Stem Cell Secretome for the Treatment of Cardiovascular Disease," Cell Stem Cell, vol. 10, No. 3, pp. 244-258, Mar. 2012.
Sayed, Nazish et al., "Transdifferentiation of Human Fibroblasts to Endothelial Cells: Role of Innate Immunity", Circulation, 131(3): 300-309, Jan. 20, 2015.
Tang, Jun-Ming et al., "Acetylcholine induces mesenchymal stem cell migration via Ca2+/PKC/ERK1/2 signal pathway," Journal of Cellular Biochemistry, vol. 113, No. 8, pp. 2704-2713, Aug. 1, 2012.
Waterman et al. "A New mesenchymal stem cell (MSC) paradigm: Polarization into a proinflammatory MSC1 or an immunosuppressive MSC2 phenotype", PLOS ONE, vol. 5, No. 4, p. e10088, Apr. 26, 2010.
Zeuner, Marie-Theres et al., "Paracrine effects of TLR4-polarised mesenchymal stromal cells are mediated by extracellular vesicles", J Transl Med, 14:34, pp. 1-4, 2016.
Karikó, K et al., "mRNA is an endogenous ligand for Toll-like receptor 3", J Biol Chem., vol. 279, No. 13, pp. 12542-12550, Mar. 26, 2004.
Yamasaki, M et al., "Neuroprotective effects of erythropoietin on glutamate and nitric oxide toxicity in primary cultured retinal ganglion cells", Brain Res., vol. 1050, No. 1-2, pp. 15-26, Jul. 19, 2005.
Jeon et al. Cobalt chloride induces neuronal differentiation of human mesenchymal stem cells through upregulation of microRNA-124a. Biochem Biophys Res Commun. 444(4):581-587 (2014).
Kauffman et al. Whole genome analysis of the action of interferon-beta. Int J Clin Pharmacol Ther. 47(5):328-357 (2009).
Zhou, Y. et al., "Glutamate as a neurotransmitter in the healthy brain", J Neural Transm, vol. 121, pp. 799-817 (2014). https://doi.org/10.1007/s00702-014-1180-8.
Basford, C.L. et al., "The functional and molecular characterisation of human embryonic stem cell-derived insulin-positive cells compared with adult pancreatic beta cells", Diabetologia, 55:358-371, 2012.
Jaishankar, Amritha et al., "Human embryonic and mesenchymal stem cells express different nuclear proteomes", Stem Cells Dev., 18(5):793-802, Jun. 2009.
Nemati, Marzieh et al., "Efficiency of Stem Cell (SC) Differentiation into Insulin- Producing Cells for Treating Diabetes: a Systematic Review", Stem Cells International, vol. 2021, Article ID 6652915, 9 pages.

* cited by examiner

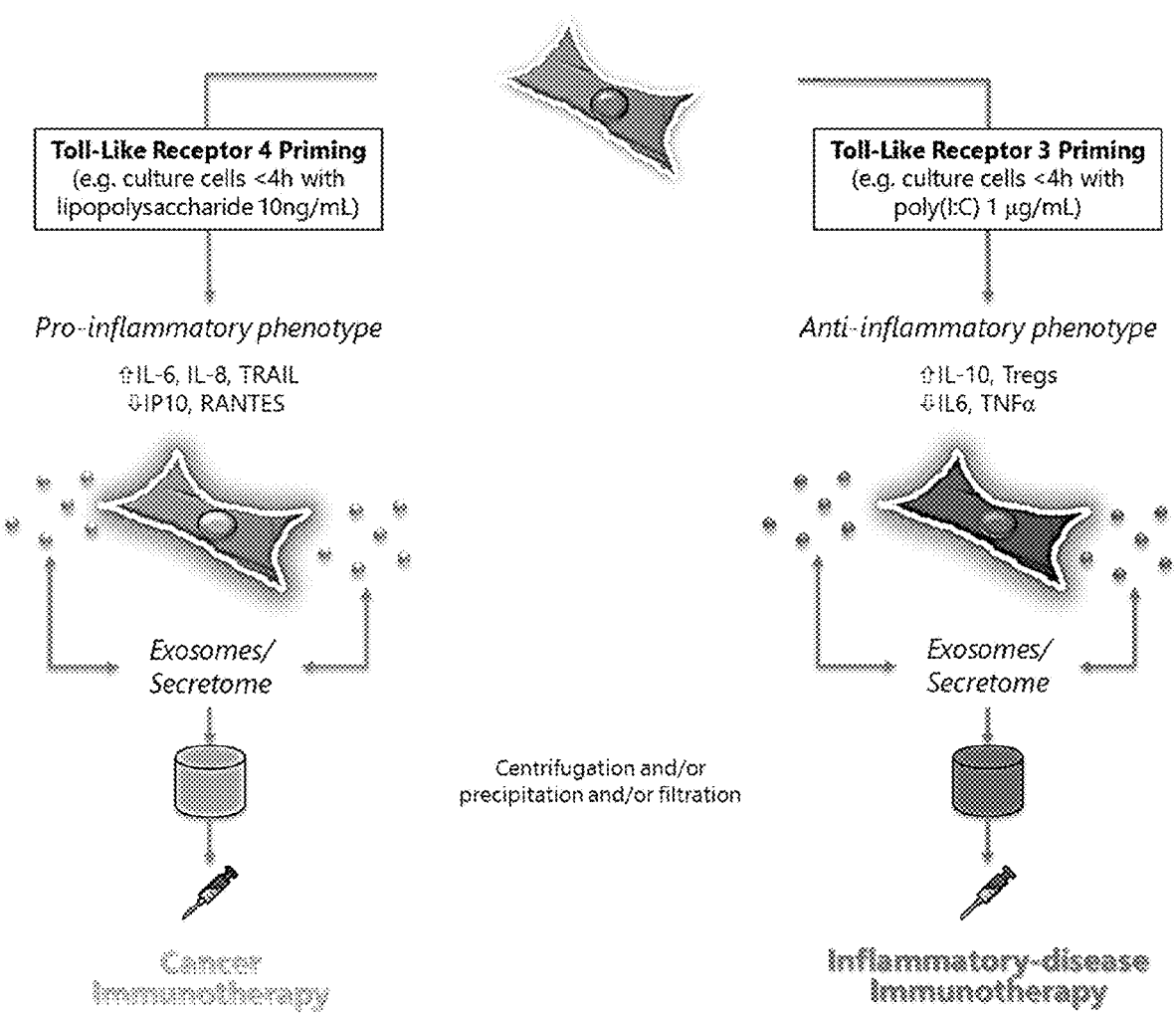

MEDIUM, METHODS, CELLS AND SECRETED FACTORS FOR STEM CELL CULTURE AND THERAPY

CROSS-REFERENCE TO RELATED APPLICATIONS

This application is a continuation of International Patent Application Number PCT/US2017/025153 filed Mar. 30, 2017, which claims priority to U.S. Patent Application No. 62/316,131 filed Mar. 31, 2016, the contents of which are incorporated herein by reference in their entirety.

BACKGROUND OF THE INVENTION

Multipotent stem cells and mesenchymal stem cells can be induced from a naive or unstimulated state into a pro-inflammatory (type 1) or an anti-inflammatory (type 2) phenotype via the selective stimulation of Toll-like receptors.

BRIEF SUMMARY OF THE INVENTION

This disclosure provides novel culture medium compositions, stem-cell culture methods, and therapy methods for the purpose of inducing, activating, or priming naïve multipotent stem cells—in some embodiments, mesenchymal stem cells—into discrete, multipotent, type 1 or type 2 cell phenotypes that selectively promote or suppress inflammation and immunity. Accordingly, the disclosure provides useful treatments in which modulation of the immune system or inflammatory responses is desirable (e.g. cancer, optic neuritis). As compared to prior methods, in the present invention, cells may be induced into a homogenous type 2 population which more efficiently migrate to disease sites and consistently express a higher level of anti-inflammatory cytokines, and so the potency and efficacy of the cells are expected to be greater. As compared to prior methods, in the present invention, cells may be induced into a homogenous type 1 population with distinctive pro-inflammatory properties and consistently higher expression of certain cytokines leading to tumor necrosis and the ability to efficiently migrate to the tumor microenvironment, so the safety, potency and efficacy of the cells is expected to be greater.

This disclosure provides novel stem-cell culture and therapy methods and culture medium compositions for the purpose of inducing, polarizing, activating, or priming discrete uniform cell phenotypes to selectively promote or suppress inflammation and immunity, providing significant advantages over known culture media and methods used in cell-based therapy. The methods and medium compositions can be used to provide more uniform and predictable ex vivo expanded and induced, polarized, activated, or primed populations of multipotent stem cells, which can be used for cell-based therapy. An advantage of the various embodiments of this disclosure is that they can be used to induce, polarize, activate, or prime cultures of multipotent stem cells into uniform and discrete phenotypes that behave in a predictable manner upon introduction into a patient. In some embodiments, the multipotent stem cells are mesenchymal stem cells.

This disclosure also provides for novel by-products of stem-cell culture, therapy methods, and medium compositions for the purpose of producing the by-products. In certain embodiments, the by-product is a conditioned media produced by the multipotent stem cells using the novel stem-cell culture methods and compositions of this disclosure. In certain embodiments, the by-product is an extracellular vesicle produced by the multipotent stem cells using the novel stem-cell culture methods and compositions of this disclosure. In some embodiments, the multipotent stem cells are mesenchymal stem cells.

In a certain embodiment, described herein, is a medium for producing an immunologically polarized multipotent stem cell population from an unstimulated multipotent stem cell population, the medium comprising: a Toll-like receptor 3 (TLR3) ligand; a second inducing agent, wherein the second inducing agent comprises a different Toll-like receptor ligand, a neurotransmitter, a neurotransmitter-like molecule, a non-erythropoietin polypeptide, or a lipid. In a certain embodiment, the second inducing agent is selected from a list consisting of: histamine, acetylcholine, glutamate, norepinephrine, epinephrine, serotonin, melatonin, lipoxin A4, alpha-melanocyte-stimulating hormone (α-MSH), and leukotriene B4. In a certain embodiment, the TLR3 ligand comprises poly(I:C), poly(A:U), or a combination thereof. In a certain embodiment, the medium further comprises i) a hypoxic condition, ii) a hypoxia mimetic, iii) erythropoietin, or iv) any combination of i), ii), or iii). In a certain embodiment, the hypoxia mimetic comprises cobalt chloride, desferrioxamine, or a combination thereof. In a certain embodiment, the medium further comprises a multipotent stem cell population. In a certain embodiment, the multipotent stem cell population comprises a mesenchymal stem cell population. In a certain embodiment, the medium produces a greater than 20-fold induction of CXCL9 mRNA than in an unstimulated multipotent stem cell population. In a certain embodiment, the medium produces a greater than 2-fold induction of any one miRNA selected from the list consisting of miR-Let 7a/d, miR-17_1, miR-222, miR-92a, and miR-1260a than in an unstimulated multipotent stem cell population. In a certain embodiment herein, is a multipotent stem cell population harvested from the medium. In a certain embodiment, the multipotent cell population comprises a mesenchymal cell population. In a certain embodiment, the multipotent cell population consists essentially of a mesenchymal cell population. In a certain embodiment, the multipotent stem cell population is for use in treating an inflammatory or autoimmune condition. In a certain embodiment herein, is a method of treating an inflammatory or autoimmune condition comprising administering to a subject a therapeutically effective amount of an immunologically polarized multipotent stem cell population harvested from the medium described in this paragraph. In a certain embodiment herein, is a method for producing an immunologically polarized multipotent stem cell population from an unstimulated multipotent stem cell population comprising contacting the unstimulated multipotent stem cell population with the medium described in this paragraph. In a certain embodiment, the multipotent stem cell population comprises a mesenchymal cell population. In a certain embodiment, the multipotent stem cell population consists essentially of a mesenchymal cell population. In a certain embodiment, the method further comprises administering to a subject a therapeutically effective amount of the immunologically polarized multipotent stem cell population described in this paragraph. In a certain embodiment herein, is a method of producing an extracellular vesicle comprising contacting an unstimulated multipotent stem cell population with the medium described in this paragraph. In a certain embodiment, the multipotent stem cell population comprises a mesenchymal stem cell population. In a certain embodiment, the multipotent stem cell population consists essentially of a mesenchymal stem cell population. In a certain embodiment, the extracellular vesicle is isolated and/or purified from the medium.

In a certain embodiment, described herein, is a medium for producing an immunologically polarized multipotent stem cell population from an unstimulated multipotent stem cell population, the medium comprising: a first inducing agent, which is a Toll-like receptor 4 (TLR4) ligand; a second inducing agent, wherein the second inducing agent comprises a different Toll-like receptor ligand from the first inducing agent, a neurotransmitter, a neurotransmitter-like molecule, a non-erythropoietin polypeptide, or a lipid. In a certain embodiment, the second inducing agent is selected from the list consisting of histamine, acetylcholine, glutamate, norepinephrine, epinephrine, serotonin, melatonin, lipoxin A4, alpha-melanocyte-stimulating hormone (α-MSH), and leukotriene B4. In a certain embodiment, the TLR4 ligand comprises lipopolysaccharide, aminoalkyl glucosaminide 4-phosphate, or a combination thereof. In a certain embodiment, the medium further comprises a i) a hypoxic condition, ii) a hypoxia mimetic, iii) erythropoietin, or iv) any combination of i), ii), or iii). In a certain embodiment, the hypoxia mimetic comprises cobalt chloride, desferrioxamine, or a combination thereof. In a certain embodiment, the medium further comprises a multipotent stem cell population. In a certain embodiment, the multipotent stem cell population comprises a mesenchymal stem cell population. In a certain embodiment, the medium produces a greater than 20-fold induction of TNFSF10 mRNA than in an unstimulated multipotent stem cell population. In a certain embodiment, the medium produces a greater than 2-fold induction of any one miRNA selected from the list consisting of miR-146, miR-155, miR-1305, miR-575, and miR-1973 than in an unstimulated multipotent stem cell population. In a certain embodiment herein, is a multipotent stem cell population harvested from the medium described in this paragraph. In a certain embodiment, the multipotent stem cell population comprises a mesenchymal stem cell population. In a certain embodiment, the multipotent stem cell population consists essentially of a mesenchymal cell population. In a certain embodiment, the multipotent stem cell population is for use in treating a tumor or a cancer. In a certain embodiment herein, is a method of treating a tumor or cancer comprising administering to a subject a therapeutically effective amount of a multipotent stem cell population harvested from the medium described in this paragraph. In a certain embodiment, the multipotent stem cell population comprises a mesenchymal cell population. In a certain embodiment, the multipotent stem cell population consists essentially of a mesenchymal cell population. In a certain embodiment herein, is a method for producing an immunologically polarized multipotent stem cell population from an unstimulated multipotent stem cell population comprising contacting the unstimulated multipotent stem cell population with the medium described in this paragraph. In a certain embodiment, the multipotent stem cell population comprises a mesenchymal stem cell population. In a certain embodiment, the multipotent stem cell population consists essentially of a mesenchymal stem cell population. In a certain embodiment, the method further comprises administering to a subject a therapeutically effective amount of the immunologically polarized multipotent stem cell population. In a certain embodiment herein, is a method of producing an extracellular vesicle comprising contacting a multipotent stem cell population with the medium described in this paragraph. In a certain embodiment, the multipotent stem cell population comprises a mesenchymal stem cell population. In a certain embodiment, the multipotent stem cell population consists essentially of a mesenchymal stem cell population. In a certain embodiment, the extracellular vesicle is isolated and/or purified from the medium.

In a certain embodiment, described herein, is an isolated and purified extracellular vesicle comprising an elevated level of any one or more of glyceraldehyde-3-phosphate dehydrogenase (GAPDH), junction plakoglobin (JUP), desmoplakin (DSP), moesin (MSN), vimentin (VIM), actin (ACTB), annexin A2 (ANXA2) proteins, or portions thereof, wherein the elevated level is compared to the level present in a naïve unstimulated mesenchymal stem cell. In a certain embodiment, the isolated and purified extracellular vesicle comprises an elevated level of any two or more of glyceraldehyde-3-phosphate dehydrogenase (GAPDH), junction plakoglobin (JUP), desmoplakin (DSP), moesin (MSN), vimentin (VIM), actin (ACTB), and annexin A2 (ANXA2). In a certain embodiment, the isolated and purified extracellular vesicle comprises an elevated level of all seven of glyceraldehyde-3-phosphate dehydrogenase (GAPDH), junction plakoglobin (JUP), desmoplakin (DSP), moesin (MSN), vimentin (VIM), actin (ACTB), or annexin A2 (ANXA2). In a certain embodiment, the isolated and purified extracellular vesicle further comprises a pharmaceutically acceptable, excipient, diluent, or carrier. In a certain embodiment, the isolated and purified extracellular vesicle is for use in treating a subject with a tumor or a cancer. In a certain embodiment herein, is a method of treating a cancer or tumor in a subject comprising administering a therapeutically effective amount of the isolated and purified extracellular vesicle described in this paragraph.

In a certain embodiment, described herein, is an isolated and purified extracellular vesicle comprising an elevated level of any one or more of myosin-1 (MYH1), myosin-2 (MTH2), myosin-7 (MYH-7), tissue factor pathway inhibitor 2 (TFPI2) proteins or portions thereof, wherein the elevated level is compared to the level present in a naïve unstimulated mesenchymal stem cell. In a certain embodiment, the isolated and purified extracellular vesicle comprises an elevated level of any two or more proteins selected from myosin-1 (MYH1), myosin-2 (MTH2), myosin-7 (MYH-7), or tissue factor pathway inhibitor 2 (TFPI2). In a certain embodiment, the isolated and purified extracellular vesicle comprises an elevated level of all four of myosin-1 (MYH1), myosin-2 (MTH2), myosin-7 (MYH-7), and tissue factor pathway inhibitor 2 (TFPI2). In a certain embodiment, the isolated and purified extracellular vesicle further comprises non-active ingredients selected from a pharmaceutically acceptable excipient, diluent, or carrier. In a certain embodiment, the isolated and purified extracellular vesicle is for use in treating a subject with a tumor or a cancer. In a certain embodiment herein, is a method of treating a cancer or tumor in a subject comprising administering a therapeutically effective amount of the isolated and purified extracellular vesicle described in this paragraph.

In certain embodiments, described herein, is a medium for producing an immunologically polarized multipotent stem cell population from an unstimulated multipotent stem cell population, the medium comprising a first and a second inducing agent, wherein the first inducing agent is a Toll-like receptor 3 (TLR3) ligand, wherein the second inducing agent is a different Toll-like receptor ligand from the first inducing agent, a neurotransmitter, a neurotransmitter-like molecule, a polypeptide that is not erythropoietin, or a lipid. In certain embodiments, the second inducing agent is histamine. In certain embodiments, the second inducing agent is acetylcholine. In certain embodiments, the second inducing agent is glutamate. In certain embodiments, the second inducing agent is norepinephrine. In certain embodiments, the second inducing agent is epinephrine. In certain embodiments, the second inducing agent is serotonin. In certain embodiments, the second inducing agent is melatonin. In certain embodiments, the second inducing agent is lipoxin A4. In certain embodiments, the second inducing agent is alpha-melanocyte-stimulating hormone. In certain embodiments, the second inducing agent is leukotriene B4. In certain embodiments, the TLR3 ligand is poly(I:C). In certain embodiments, the TLR3 ligand is poly(A:U). In certain embodiments, the medium further comprises a third inducing agent, wherein the third inducing agent comprises a hypoxic condition, a hypoxia mimetic, or erythropoietin. In certain embodiments, the hypoxia mimetic is cobalt chloride. In certain embodiments, the hypoxia mimetic is desferrioxamine. In certain embodiments, the medium further comprises a fourth inducing agent, wherein the fourth inducing agent is different than the third inducing agent and comprises a hypoxic condition, a hypoxia mimetic, or erythropoietin. In certain embodiments, the hypoxia mimetic is cobalt chloride. In certain embodiments, the hypoxia mimetic is desferrioxamine. In certain embodiments, the medium further comprises a multipotent stem cell population. In certain embodiments, the multipotent stem cell population is an unstimulated multipotent stem cell population. In certain embodiments, the multipotent stem cell population is a stimulated multipotent stem cell population. In certain embodiments, the multipotent stem cell population is an induced multipotent stem cell population. In certain embodiments, the multipotent stem cell population is an adult multipotent stem cell population. In certain embodiments, the multipotent stem cell population is a human multipotent stem cell population. In certain embodiments, the multipotent stem cell population is a mesenchymal stem cell population. In certain embodiments, the medium does not comprise serum of human or animal origin. In certain embodiments, the medium is able to produce a greater than 20-fold induction of CXCL9 mRNA in the stimulated stem cell population than in an unstimulated multipotent stem cell. In certain embodiments, the medium is able to produce a greater than 30-fold induction of CXCL9 mRNA than in an unstimulated multipotent stem cell. In certain embodiments, the medium is able to produce a greater than 50-fold induction of CXCL9 mRNA than in an unstimulated multipotent stem cell. In certain embodiments, the immunologically polarized multipotent stem cell population described in this paragraph is for use in treating rheumatoid arthritis. In certain embodiments, the immunologically polarized multipotent stem cell population described in this paragraph is for use in treating diabetic neuropathy. In certain embodiments, the immunologically polarized multipotent stem cell population described in this paragraph is for use in treating Crohn's disease. In certain embodiments, the immunologically polarized multipotent stem cell population described in this paragraph is for use in treating acute lung injury. In certain embodiments, the immunologically polarized multipotent stem cell population described in this paragraph is for use in treating multiple sclerosis. In certain embodiments, the immunologically polarized multipotent stem cell population described in this paragraph is for use in treating acute optic neuritis. In certain embodiments, the immunologically polarized multipotent stem cell population described in this paragraph is for use in treating Krabbe disease.

In certain embodiments, described herein, is a medium for producing an immunologically polarized multipotent stem cell population from an unstimulated multipotent stem cell population, the medium comprising a first and a second inducing agent, wherein the first inducing agent is a Toll-like receptor 4 (TLR4) ligand, wherein the second inducing agent is a different Toll-like receptor ligand from the first inducing agent, a neurotransmitter, a neurotransmitter-like molecule, a polypeptide that is not erythropoietin, or a lipid. In certain embodiments, the second inducing agent is histamine. In certain embodiments, the second inducing agent is acetylcholine. In certain embodiments, the second inducing agent is glutamate. In certain embodiments, the second inducing agent is norepinephrine. In certain embodiments, the second inducing agent is epinephrine. In certain embodiments, the second inducing agent is serotonin. In certain embodiments, the second inducing agent is melatonin. In certain embodiments, the second inducing agent is lipoxin A4. In certain embodiments, the second inducing agent is alpha-melanocyte-stimulating hormone. In certain embodiments, the second inducing agent is leukotriene B4. In certain embodiments, the TLR4 ligand is LPS. In certain embodiments, the TLR4 ligand is aminoalkyl glucosaminide 4-phosphate. In certain embodiments, the medium further comprises a third inducing agent, wherein the third inducing agent comprises a hypoxic condition, a hypoxia mimetic, or erythropoietin. In certain embodiments, the hypoxia mimetic is cobalt chloride. In certain embodiments, hypoxia mimetic is desferrioxamine. In certain embodiments, the medium further comprises a fourth inducing agent, wherein the fourth inducing agent is different than the third inducing agent and comprises a hypoxic condition, a hypoxia mimetic, or erythropoietin. In certain embodiments, the hypoxia mimetic is cobalt chloride. In certain embodiments, the hypoxia mimetic is desferrioxamine. In certain embodiments, the medium further comprises a multipotent stem cell population. In certain embodiments, the multipotent stem cell population is an unstimulated multipotent stem cell population. In certain embodiments, the multipotent stem cell population is a stimulated multipotent stem cell population. In certain embodiments, the multipotent stem cell population is an induced multipotent stem cell population. In certain embodiments, the multipotent stem cell population is an adult multipotent stem cell population. In certain embodiments, the multipotent stem cell population is a human multipotent stem cell population. In certain embodiments, the multipotent stem cell population is a mesenchymal stem cell population. In certain embodiments, the medium does not comprise serum of human or animal origin. In certain embodiments, the medium is able to produce a greater than 20-fold induction of TNFSF10 mRNA in the stimulated stem cell population than in an unstimulated multipotent stem cell. In certain embodiments, the medium is able to produce a greater than 30-fold induction of TNFSF10 mRNA than in an unstimulated multipotent stem cell. In certain embodiments, the medium is able to produce a greater than 50-fold induction of TNFSF10 mRNA than in an unstimulated multipotent stem cell. In certain embodiments, the immunologically polarized multipotent stem cell population described in this paragraph is for use in treating ovarian cancer. In certain embodiments, the immunologically polarized multipotent stem cell population described in this paragraph is for use in treating breast cancer.

In certain embodiments, described herein, is a method of producing an immunologically polarized multipotent stem cell population from an unstimulated multipotent stem cell population comprising: contacting an unstimulated multipotent stem cell population with a medium comprising a first and a second inducing agent, wherein the first inducing agent is a Toll-like receptor 3 (TLR3) ligand, wherein the second inducing agent is a neurotransmitter, a polypeptide that is not erythropoietin, or a lipid. In certain embodiments, the second inducing agent is histamine. In certain embodiments, the second inducing agent is acetylcholine. In certain embodiments, the second inducing agent is glutamate. In certain embodiments, the second inducing agent is norepinephrine. In certain embodiments, the second inducing agent is epinephrine. In certain embodiments, the second inducing agent is serotonin. In certain embodiments, the second inducing agent is melatonin. In certain embodiments, the second inducing agent is lipoxin A4. In certain embodiments, the second inducing agent is alpha-melanocyte-stimulating hormone. In certain embodiments, the second inducing agent is leukotriene B4. In certain embodiments, the TLR3 ligand is poly(I:C). In certain embodiments, the TLR3 ligand is poly(A:U). In certain embodiments, the medium further comprises a third inducing agent, wherein the third inducing agent comprises a hypoxic condition, a hypoxia mimetic, erythropoietin, or any combination thereof. In certain embodiments, the hypoxia mimetic is cobalt chloride. In certain embodiments, the hypoxia mimetic is desferrioxamine. In certain embodiments, the medium further comprises a fourth inducing agent, wherein the fourth inducing agent is different than the third inducing agent and comprises a hypoxic condition, a hypoxia mimetic, erythropoietin, or any combination thereof. In certain embodiments, the hypoxia mimetic is cobalt chloride. In certain embodiments, the hypoxia mimetic is desferrioxamine. In certain embodiments, the multipotent stem cell population is an induced multipotent stem cell population. In certain embodiments, the multipotent stem cell population is an adult multipotent stem cell population. In certain embodiments, the multipotent stem cell population is a human multipotent stem cell population. In certain embodiments, the multipotent stem cell population is a mesenchymal stem cell population. In certain embodiments, the medium does not comprise serum of human or animal origin. In certain embodiments, the method is able to produce a greater than 20-fold induction of CXCL9 mRNA in the induced multipotent stem cell population than in an unstimulated multipotent stem cell population. In certain embodiments, the method is able to produce a greater than 30-fold induction of CXCL9 mRNA than in an unstimulated multipotent stem cell population. In certain embodiments, the method is able to produce a greater than 50-fold induction of CXCL9 mRNA than in an unstimulated multipotent stem cell population. In certain embodiments, described herein, is a polarized multipotent stem cell population produced by the preceding method. In certain embodiments, the polarized multipotent stem cell population produced by the preceding method is for use in treating rheumatoid arthritis. In certain embodiments, the polarized multipotent stem cell population produced by the preceding method is for use in treating diabetic neuropathy. In certain embodiments, the polarized multipotent stem cell population produced by the preceding method is for use in treating Crohn's disease. In certain embodiments, the polarized multipotent stem cell population produced by the preceding method is for use in treating acute lung injury. In certain embodiments, the polarized multipotent stem cell population produced by the preceding method is for use in treating multiple sclerosis. In certain embodiments, the polarized multipotent stem cell population produced by the preceding method is for use in treating acute optic neuritis. In certain embodiments, the polarized multipotent stem cell population produced by the preceding method is for use in treating Krabbe disease.

In certain embodiments, described herein, is method of producing an immunologically polarized multipotent stem cell population from an unstimulated multipotent stem cell population comprising: contacting an unstimulated multipotent stem cell population with a medium comprising a first and a second inducing agent, wherein the first inducing agent is a Toll-like receptor 4 (TLR4) ligand, wherein the second inducing agent is a neurotransmitter, a polypeptide that is not erythropoietin, or a lipid. In certain embodiments, the second inducing agent is histamine. In certain embodiments, the second inducing agent is acetylcholine. In certain embodiments, the second inducing agent is glutamate. In certain embodiments, the second inducing agent is norepinephrine. In certain embodiments, the second inducing agent is epinephrine. In certain embodiments, the second inducing agent is serotonin. In certain embodiments, the second inducing agent is melatonin. In certain embodiments, the second inducing agent is lipoxin A4. In certain embodiments, the second inducing agent is alpha-melanocyte-stimulating hormone. In certain embodiments, the second inducing agent is leukotriene B4. In certain embodiments, the TLR4 ligand is LPS. In certain embodiments, the TLR4 ligand is aminoalkyl glucosaminide 4-phosphate. In certain embodiments, the medium further comprises a third inducing agent, wherein the third inducing agent comprises a hypoxic condition, a hypoxia mimetic, erythropoietin, or any combination thereof. In certain embodiments, the hypoxia mimetic is cobalt chloride. In certain embodiments, the hypoxia mimetic is desferrioxamine. In certain embodiments, the medium further comprises a fourth inducing agent, wherein the fourth inducing agent is different than the third inducing agent and comprises a hypoxic condition, a hypoxia mimetic, erythropoietin, or any combination thereof. In certain embodiments, the hypoxia mimetic is cobalt chloride. In certain embodiments, the hypoxia mimetic is desferrioxamine. In certain embodiments, the multipotent stem cell population is an induced multipotent stem cell population. In certain embodiments, the multipotent stem cell population is an adult multipotent stem cell population. In certain embodiments, the multipotent stem cell population is a human multipotent stem cell population. In certain embodiments, the multipotent stem cell population is a mesenchymal stem cell population. In certain embodiments, the medium does not comprise serum of human or animal origin. In certain embodiments, the method is able to produce a greater than 20-fold induction of TNFSF10 mRNA in the induced multipotent stem cell population than in an unstimulated multipotent stem cell population. In certain embodiments, the method is able to produce a greater than 30-fold induction of TNFSF10 mRNA than in an unstimulated multipotent stem cell population. In certain embodiments, the method is able to produce a greater than 50-fold induction of TNFSF10 mRNA than in an unstimulated multipotent stem cell population. In certain embodiments, described herein, is a polarized multipotent stem cell population produced by the preceding method. In certain embodiments, the polarized multipotent stem cell population produced by the preceding method is for use in treating ovarian cancer. In certain embodiments, the polarized multipotent stem cell population produced by the preceding method is for use in treating breast cancer.

In certain embodiments, described herein, is a factor that has been secreted from a stimulated multipotent stem cell population. In certain embodiments, the factor has been isolated from a medium in contact with the stimulated multipotent stem cell. In certain embodiments, the isolation method comprises any one or more of: centrifugation, extraction, precipitation, filtration, and freezing. In certain embodiments, the factor is pro-inflammatory. In certain embodiments, the factor is anti-inflammatory. In certain embodiments, the factor is an extracellular vesicle. In certain embodiments, the factor is a cytokine. In certain embodiments, the factor is a chemokine. In certain embodiments, the factor is an miRNA. In certain embodiments, the stimulated multipotent stem cell population has been stimulated by a Toll-like receptor 3 (TLR3) ligand. In certain embodiments, the TLR3 ligand is poly(I:C). In certain embodiments, the TLR3 ligand is poly(A:U). In certain embodiments, the stimulated multipotent stem cell population has been stimulated by a Toll-like receptor 4 (TLR4) ligand. In certain embodiments, the TLR4 ligand is lipopolysaccharide. In certain embodiments, the TLR4 ligand is aminoalkyl glucosaminide 4-phosphate. In certain embodiments, the inducing agent is a hypoxic condition or a hypoxia mimetic. In certain embodiments, the hypoxic condition is a hypoxia mimetic. In certain embodiments, the hypoxia mimetic is cobalt chloride. In certain embodiments, the hypoxia mimetic is desferrioxamine. In certain embodiments, the stimulated multipotent stem cell population has been stimulated by erythropoietin. In certain embodiments, the stimulated multipotent stem cell population has been stimulated by histamine. In certain embodiments, the stimulated multipotent stem cell population has been stimulated by acetylcholine. In certain embodiments, the stimulated multipotent stem cell population has been stimulated by glutamate. In certain embodiments, the stimulated multipotent stem cell population has been stimulated by epinephrine. In certain embodiments, the stimulated multipotent stem cell population has been stimulated by serotonin. In certain embodiments, the stimulated multipotent stem cell population has been stimulated by lipoxin A4. In certain embodiments, the stimulated multipotent cell population has been stimulated by alpha-melanocyte-stimulating hormone. In certain embodiments, the stimulated multipotent stem cell population has been stimulated by leukotriene B4. In certain embodiments, the stimulated multipotent stem cell population has been stimulated in the absence of serum of human or animal origin. In certain embodiments, the stimulated multipotent cell population is an induced multipotent stem cell population. In certain embodiments, the stimulated multipotent cell population is an adult multipotent stem cell population. In certain embodiments, the stimulated multipotent cell population is a human multipotent stem cell population. In certain embodiments, the stimulated multipotent stem cell population is a mesenchymal stem cell population. In certain embodiments, the stimulated multipotent cell population is a type 1 mesenchymal stem cell population. In certain embodiments, the type 1 mesenchymal stem cell population expresses TNFSF10 mRNA at a higher level than an unstimulated mesenchymal stem cell population. In certain embodiments, the stimulated multipotent cell population is a type 2 mesenchymal stem cell population. In certain embodiments, the type 2 mesenchymal stem cell population expresses CXCL9 mRNA at a higher level than an unstimulated mesenchymal stem cell population. In certain embodiments, the factor is for use in treating rheumatoid arthritis. In certain embodiments, the factor is for use in treating diabetic neuropathy. In certain embodiments, the factor is for use in treating Crohn's disease. In certain embodiments, the factor is for use in treating acute lung injury. In certain embodiments, the factor is for use in treating multiple sclerosis. In certain embodiments, the factor is for use in treating acute optic neuritis. In certain embodiments, the factor is for use in treating method for use in treating Krabbe disease.

In certain embodiments, described herein, is an extracellular vesicle secreted from a mesenchymal stem cell population that has been stimulated with a medium comprising a TLR4 ligand. In certain embodiments, the medium comprises erythropoietin and a hypoxic condition or a hypoxia mimetic. In certain embodiments, the extracellular vesicle is for use in treating ovarian cancer. In certain embodiments, the extracellular vesicle is for use in treating breast cancer.

In certain embodiments, described herein, is an extracellular vesicle that has been secreted from a mesenchymal stem cell population that has been stimulated with a medium comprising a TLR3 ligand. In certain embodiments, the medium comprises erythropoietin and a hypoxic condition or a hypoxia mimetic. In certain embodiments, the extracellular vesicle is for use in treating rheumatoid arthritis. In certain embodiments, the extracellular vesicle is for use in treating diabetic neuropathy. In certain embodiments, the extracellular vesicle is for use in treating Crohn's disease. In certain embodiments, the extracellular vesicle is for use in treating acute lung injury. In certain embodiments, the extracellular vesicle is for use in treating multiple sclerosis. In certain embodiments, the extracellular vesicle is for use in treating acute optic neuritis. In certain embodiments, the extracellular vesicle is for use in treating Krabbe disease.

In certain embodiments, described herein, is a method for producing a factor secreted from a stimulated multipotent stem cell population comprising: contacting an unstimulated multipotent stem cell population with a medium comprising an inducing agent; incubating the medium with the unstimulated multipotent stem cell population; and harvesting the medium; wherein incubation with the medium produces a stimulated multipotent stem cell population from the unstimulated multipotent stem cell population, and results in the secretion of at least one factor from the stimulated multipotent stem cell population. In certain embodiments, the method further comprises isolating the factor from the medium. In certain embodiments, isolating comprises any one or more of: centrifugation, extraction, precipitation, filtration, and freezing. In certain embodiments, the factor is pro-inflammatory. In certain embodiments, the factor is anti-inflammatory. In certain embodiments, the factor is an extracellular vesicle. In certain embodiments, the factor is a cytokine. In certain embodiments, the factor is a chemokine. In certain embodiments, the factor is an miRNA. In certain embodiments, the inducing agent is a Toll-like receptor 3 (TLR3) ligand. In certain embodiments, the TLR3 ligand is poly(I:C). In certain embodiments, the TLR3 ligand is poly(A:U). In certain embodiments, the inducing agent is a Toll-like receptor 4 (TLR4) ligand. In certain embodiments, the TLR4 ligand is lipopolysaccharide. In certain embodiments, the TLR4 ligand is aminoalkyl glucosaminide 4-phosphate. In certain embodiments, the inducing agent is a hypoxic condition or a hypoxia mimetic. In certain embodiments, the hypoxia mimetic is cobalt chloride. In certain embodiments, the hypoxia mimetic is desferrioxamine. In certain embodiments, the inducing agent is erythropoietin. In certain embodiments, the inducing agent is histamine. In certain embodiments, the inducing agent is acetylcholine. In certain embodiments, the inducing agent is glutamate. In certain embodiments, the inducing agent is epinephrine. In certain embodiments, the inducing agent is serotonin. In certain embodiments, the inducing agent is lipoxin A4. In certain embodiments, the inducing agent is alpha-melanocyte-stimulating hormone. In certain embodiments, the inducing agent is leukotriene B4. In certain embodiments, the medium does not contain serum of human or animal origin. In certain embodiments, the stimulated multipotent cell population is an induced multipotent stem cell population. In certain embodiments, the stimulated multipotent cell population is an adult multipotent stem cell population. In certain embodiments, the stimulated multipotent cell population is a human multipotent stem cell population. In certain embodiments, the stimulated multipotent stem cell is a mesenchymal stem cell population. In certain embodiments, the stimulated multipotent cell is a type 1 mesenchymal stem cell population. In certain embodiments, the type 1 mesenchymal stem cell population expresses TNFSF10 mRNA at a higher level than an unstimulated mesenchymal stem cell population. In certain embodiments, the stimulated multipotent cell population is a type 2 mesenchymal stem cell population. In certain embodiments, the type 2 mesenchymal stem cell population expresses CXCL9 at a higher level than an unstimulated mesenchymal stem cell population. In certain embodiments, the factor is for use in treating ovarian cancer. In certain embodiments, the factor is for use in treating breast cancer. In certain embodiments, the factor is for use in treating rheumatoid arthritis. In certain embodiments, the factor is for use in treating diabetic neuropathy. In certain embodiments, the factor is for use in treating Crohn's disease. In certain embodiments, the factor is for use in treating acute lung injury. In certain embodiments, the factor is for use in treating multiple sclerosis. In certain embodiments, the factor is for use in treating acute optic neuritis. In certain embodiments, the factor is for use in treating Krabbe disease.

In certain embodiments, described herein, is method for producing an extracellular vesicle secreted from a mesenchymal stem cell population comprising: contacting an unstimulated mesenchymal stem cell population with a medium comprising a TLR4 ligand; incubating the medium with the unstimulated mesenchymal stem cell population; and harvesting the medium; wherein incubation with the medium produces a stimulated mesenchymal stem cell population from the unstimulated mesenchymal stem cell population, and results in the secretion of at least one extracellular vesicle from the stimulated mesenchymal stem cell population. In certain embodiments, the medium comprises erythropoietin and a hypoxic condition or a hypoxia mimetic. In certain embodiments, the extracellular vesicle is for use in treating ovarian cancer.

In certain embodiments, described herein, is a method for producing an extracellular vesicle secreted from a mesenchymal stem cell population comprising: contacting an unstimulated mesenchymal stem cell population with a medium comprising a TLR3 ligand; incubating the medium with the unstimulated mesenchymal stem cell population; and harvesting the medium; wherein incubation with the medium produces a stimulated mesenchymal stem cell population from the unstimulated mesenchymal stem cell population, and results in the secretion of at least one extracellular vesicle from the stimulated mesenchymal stem cell population. In certain embodiments, the medium comprises erythropoietin and a hypoxic condition or a hypoxia mimetic. In certain embodiments, the extracellular vesicle is for use in treating rheumatoid arthritis. In certain embodiments, the extracellular vesicle is for use in treating diabetic neuropathy. In certain embodiments, the extracellular vesicle is for use in treating Crohn's disease. In certain embodiments, the extracellular vesicle is for use in treating acute lung injury. In certain embodiments, the extracellular vesicle is for use in treating multiple sclerosis. In certain embodiments, the extracellular vesicle is for use in treating acute optic neuritis. In certain embodiments, the extracellular vesicle is for use in treating Krabbe disease.

BRIEF DESCRIPTION OF THE SEVERAL VIEWS OF THE DRAWINGS

FIG. 2 illustrates a schematic flow chart of the therapeutic methods described herein using extracellular vesicles and secreted factors.

DETAILED DESCRIPTION OF THE INVENTION

Figure 1:
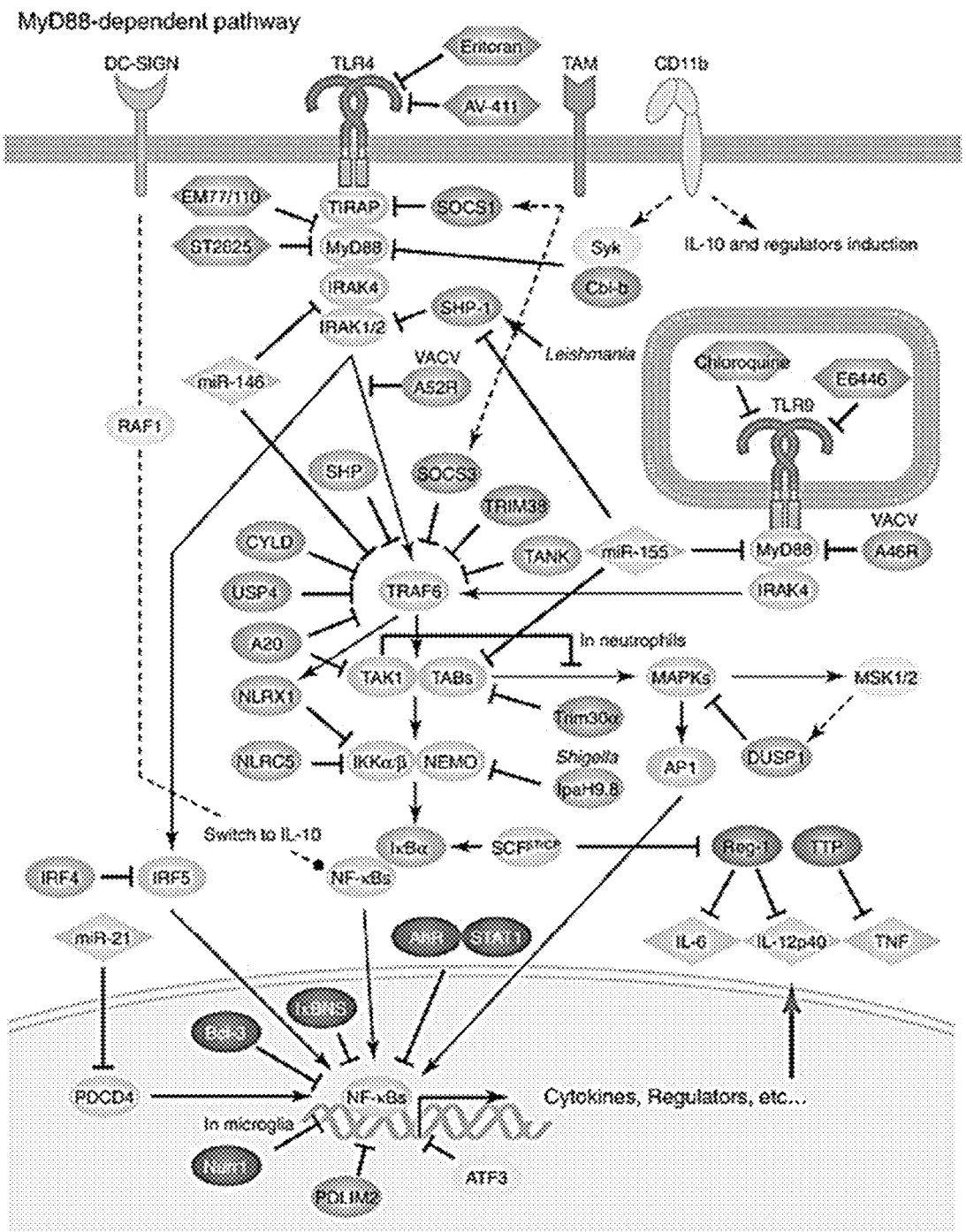
FIG. 1 illustrates the MyD88-dependent Toll-like receptor pathway.

The methods described herein are useful for inducing multipotent stem cells to possess either pro-inflammatory or anti-inflammatory characteristics. The combination of Toll-like receptor (TLR) engagement (TLR4 for pro-inflammatory characteristics; TLR3 for anti-inflammatory characteristics) and a second agent produces stronger phenotypes than by using TLR engagement alone. These stronger phenotypes (either pro- or anti-inflammatory) are useful therapeutically. For example, pro-inflammatory multipotent stem cells possess utility in fighting neoplasms (such as tumors or cancers); anti-inflammatory multipotent stem cells possess utility in fighting inflammatory or autoimmune disorders.

In certain embodiments, described herein, is a medium for producing an immunologically polarized multipotent stem cell population from an unstimulated multipotent stem cell population, the medium comprising a first and a second inducing agent, wherein the first inducing agent is a Toll-like receptor 3 (TLR3) ligand, wherein the second inducing agent is a different Toll-like receptor ligand from the first inducing agent, a neurotransmitter, a neurotransmitter-like molecule, a polypeptide that is not erythropoietin, or a lipid. In certain embodiments, described herein, is a medium for producing an immunologically polarized multipotent stem cell population from an unstimulated multipotent stem cell population, the medium comprising a first and a second inducing agent, wherein the first inducing agent is a Toll-like receptor 4 (TLR4) ligand, wherein the second inducing agent is a different Toll-like receptor ligand from the first inducing agent, a neurotransmitter, a neurotransmitter-like molecule, a polypeptide that is not erythropoietin, or a lipid. In certain embodiments, described herein, is a method of producing an immunologically polarized multipotent stem cell population from an unstimulated multipotent stem cell population comprising: contacting an unstimulated multipotent stem cell population with a medium comprising a first and a second inducing agent, wherein the first inducing agent is a Toll-like receptor 3 (TLR3) ligand, wherein the second inducing agent is a neurotransmitter, a polypeptide that is not erythropoietin, or a lipid. In certain embodiments, described herein, is a method of producing an immunologically polarized multipotent stem cell population from an unstimulated multipotent stem cell population comprising: contacting an unstimulated multipotent stem cell population with a medium comprising a first and a second inducing agent, wherein the first inducing agent is a Toll-like receptor 4 (TLR4) ligand, wherein the second inducing agent is a neurotransmitter, a polypeptide that is not erythropoietin, or a lipid. In certain embodiments, described herein, is a factor that has been secreted from a stimulated multipotent stem cell population. In certain embodiments, described herein, is an extracellular vesicle secreted from a mesenchymal stem cell population that has been stimulated with a medium comprising a TLR4 ligand. In certain embodiments, described herein, is an extracellular vesicle that has been secreted from a mesenchymal stem cell population that has been stimulated with a medium comprising a TLR3 ligand. In certain embodiments, the medium comprises erythropoietin and a hypoxic condition or a hypoxia mimetic. In certain embodiments, described herein, is a method for producing a factor secreted from a stimulated multipotent stem cell population comprising: contacting an unstimulated multipotent stem cell population with a medium comprising an inducing agent; incubating the medium with the unstimulated multipotent stem cell population; and harvesting the medium; wherein incubation with the medium produces a stimulated multipotent stem cell population from the unstimulated multipotent stem cell population, and results in the secretion of at least one factor from the stimulated multipotent stem cell population. In certain embodiments, described herein, is method for producing an extracellular vesicle secreted from a mesenchymal stem cell population comprising: contacting an unstimulated mesenchymal stem cell population with a medium comprising a TLR4 ligand; incubating the medium with the unstimulated mesenchymal stem cell population; and harvesting the medium; wherein incubation with the medium produces a stimulated mesenchymal stem cell population from the unstimulated mesenchymal stem cell population, and results in the secretion of at least one extracellular vesicle from the stimulated mesenchymal stem cell population. In certain embodiments, described herein, is a method for producing an extracellular vesicle secreted from a mesenchymal stem cell population comprising: contacting an unstimulated mesenchymal stem cell population with a medium comprising a TLR3 ligand; incubating the medium with the unstimulated mesenchymal stem cell population; and harvesting the medium; wherein incubation with the medium produces a stimulated mesenchymal stem cell population from the unstimulated mesenchymal stem cell population, and results in the secretion of at least one extracellular vesicle from the stimulated mesenchymal stem cell population. In certain embodiments, the medium comprises erythropoietin and a hypoxic condition or a hypoxia mimetic.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, unless otherwise indicated, the term "about" refers to an amount that is near the stated amount, for example by 10%, 5%, or 1%.

The term "multipotent stem cell" means a cell which is capable of giving rise to multiple different types of cells. The term "mesenchymal stem cell" means a stem cell originally derived from the mesenchyme. The term refers to a cell which is capable of differentiating into at least two or more of an osteoblast, a chondrocyte, an adipocyte, or a myocyte. Mesenchymal stem cells (MSC) are isolated from any type of adult tissue. Typically mesenchymal stem cells are isolated from bone marrow, adipose tissue, umbilical cord, or peripheral blood. In a preferred aspect, MSCs are obtained from bone marrow or lipoaspirates, which are obtained from adipose tissue. The term "multipotent" or "pluripotent" also encompasses induced multipotent stem cells or induced pluripotent stem cells, or cells that have been induced to a pluripotent stage using any chemical or genetic means. In certain embodiments, the multipotent or pluripotent stem cells of the disclosure are mesenchymal stem cells.

The term "biological activity" refers to one or more of transcription; translation; post-translational protein modifications, such as phosphorylation, acetylation, or degradation; secretion; cell division; apoptosis; or cell motility. A substance that induces biological activity will increase or decrease any of these biological activities.

The term "population" with reference to the multipotent and mesenchymal stem cells described herein refers to a plurality of cells which are molecularly identical or highly similar. A population can be isolated from a human tissue or grown and expanded in culture. Any population provided herein can "consist essentially" of the recited cells such as multipotent stem cells or mesenchymal stem cells. As used herein "consist essentially" means that the cell population is substantially pure from a cellular composition perspective. For example, the cells can be greater than about 80%, 90%, 95%, 97%, 98%, or 99% pure.

The term "cellular therapy" or "cell-based therapy" means the transplantation of human or animal cells to prevent, treat, or ameliorate one or more symptoms associated with a disease or disorder, such as, but not limited to, the replacement or repair of damaged tissues or organs, the modulation of immune reactions and the reduction of inflammatory symptoms and cancers. Cellular therapy can be achieved by administering a therapeutically effective amount of a stem cell-multipotent or mesenchymal-cll harvested from an inducing medium.

The term "subject" refers to an animal, preferably a mammal including non-primates (e.g., a cow, pig, horse, cat, dog, rat, or mouse) or a primate (e.g., a monkey or a human). In certain embodiments, the subject is a human.

The term "hypoxic condition" or "hypoxia" refers to culturing cells or medium under conditions that are oxygen depleted compared to normal physiological oxygen levels of about 11%.

The terms "treat," "treatment," and "treating" when used directly in reference to a patient or subject mean the amelioration of one or more symptoms associated with a disorder including, but not limited to, any cancer, any tumor or neoplasm, an inflammatory disorder, an autoimmune disease or an immunologically mediated disease including rejection of transplanted organs and tissues, where the amelioration results from the administration of the immunomodulatory (i.e. immunologically polarized) cells yielded by the invention, or a pharmaceutical composition comprising immunomodulatory cells yielded by the invention, to a subject in need of such treatment.

The term "unstimulated" or "naive" refers to a cell population that has been untreated, unpolarized, or uninduced by the methods of this disclosure. Primary isolated mesenchymal stem cells that are fresh or frozen are considered unstimulated or naive. Cells that have been previously treated with a compound or composition that lacks at least one of a toll-like receptor ligand, erythropoietin, hypoxia, or a hypoxia mimetic are considered unstimulated.

The term "autoimmune disorder" refers to a condition in a subject characterized by cellular, tissue, and/or organ injury caused by an immunological reaction of the subject to its own cells, tissues, and/or organs.

The term "inflammatory disease" refers to a condition marked by increased activation of immune cells, secretion of cytokines, chemokines, or other factors that lead to immune cell activation or recruitment.

The term "extracellular vesicles" refers to cell-derived vesicles that are present in eukaryotic fluids, including blood, lymph, urine, saliva and conditioned medium of cell cultures. These extracellular vesicles are derived from cellular endosomal and plasma membranes, and can comprise DNAs, RNAs (including miRNAs), proteins, polypeptides, lipids, and small molecules. Extracellular vesicles are cell-derived small vesicles and include exosomes, microvesicles, and apoptotic bodies. In certain embodiments, the extracellular vesicles comprise, consist, or consist essentially of exosomes.

In certain embodiments, the methods and compositions of matter disclosed herein are for the treatment of diseases. In certain embodiments, the methods and compositions of matter disclosed herein are for the treatment of human diseases. In certain embodiments, the methods and compositions of matter disclosed herein are for the treatment of veterinary diseases. In certain embodiments, the methods and compositions of matter disclosed herein are for the treatment of non-human animals. In certain embodiments, the non-human animal is a dog, cat, horse, cow, pig, sheep, or goat.

Medium

In certain embodiments, the medium described herein is for use in culturing cells, stem cells, multipotent stem cells, and mesenchymal stem cells of human or other animal origin. In certain embodiments, the medium described herein is for producing a distinct phenotype in cells, stem cells, multipotent stem cells, or mesenchymal stem cells of human or other animal origin. In certain embodiments, the medium described herein comprises standard medium components for cell culture in addition to the components specifically described herein. For example, in certain non-limiting embodiments, the medium comprises vitamins, minerals, salts, sugars, amino acids, pyruvate, hormones, human serum, fetal bovine serum, fetal calf serum, lipids, proteins, dyes, pH buffers, and combinations thereof. In certain embodiments, the medium is a concentrated culture supplement. In certain embodiments, the medium is concentrated at least 2×. In certain embodiments, the medium is a concentrated at least 10×. In certain embodiments, the medium is a concentrated at least 100×. In certain embodiments, the medium is a dry powder formulation that is rehydrated by the addition of any suitable aqueous solvent such as water, by way of non-limiting example. In certain embodiments, the medium is sterile. In certain embodiments, the medium is supplied prepackaged in any suitable container. In certain embodiments, the medium is sterile filtered. In certain embodiments, the medium can contain formulations of standard culture medium such as MEM, DMEM, or RPMI, by way of non-limiting example. In certain embodiments, the medium does not comprise serum of human or other animal origin.

TLR4 Ligand

In certain embodiments, disclosed herein is a medium for producing an immunologically polarized multipotent stem cell population from an unstimulated multipotent stem cell population, the medium comprising a first and a second inducing agent, wherein the first inducing agent comprises a Toll-like receptor (TLR) ligand, and the second inducing agent comprises a molecule with biological activity. In certain embodiments, the TLR ligand comprises a Toll-like receptor 4 (TLR4) ligand. In certain embodiments, the TLR4 ligand comprises lipopolysaccharide. In certain embodiments, the TLR4 ligand comprises aminoalkyl glucosaminide 4-phosphate. In certain embodiments, the TLR4 ligand is at a concentration from about 10 pg/mL to about 10 µg/mL, from about 100 pg/mL to about 10 µg/mL, from about 1 ng/mL to about 1 µg/mL, from about 5 ng/mL to about 1 µg/mL, from about 10 ng/mL to about 1 µg/mL, from about 100 ng/mL to about 1 µg/mL, from about 5 ng/mL to about 50 ng/mL, or from about 5 ng/mL to about 25 ng/mL. In certain embodiments, the TLR4 ligand is present at a concentration of at least 10 pg/mL. In certain embodiments, the TLR4 ligand is present at a concentration of at least 100 pg/mL. In certain embodiments, the TLR4 ligand is present at a concentration of at least 1 ng/mL. In certain embodiments, the TLR4 ligand is present at a concentration of at least 10 ng/mL. In certain embodiments, the TLR4 ligand is present at a concentration of at least 100 ng/mL. In certain embodiments, the TLR4 ligand is present at a concentration of at least 1 µg/mL. In certain embodiments, the TLR4 ligand is present at a concentration of at least 10 µg/mL. In certain embodiments, the TLR4 ligand is present at a concentration of less than 1 g/mL. In certain embodiments, the TLR4 ligand is present at a concentration of less than 100 mg/mL. In certain embodiments, the TLR4 ligand is present at a concentration of less than 10 mg/mL. In certain embodiments, the TLR4 ligand is present at a concentration of less than 1 mg/mL. In certain embodiments, the TLR4 ligand is present at a concentration of less than 500 µg/mL. In certain embodiments, the TLR4 ligand is present at a concentration of less than 200 µg/mL. In certain embodiments, the TLR4 ligand is present at a concentration of less than 100 µg/mL.

TLR3 Ligand

In certain embodiments, disclosed herein, is a medium for producing an immunologically polarized multipotent stem cell population from an unstimulated multipotent stem cell population, the medium comprising a first and a second inducing agent, wherein the first inducing agent comprises a Toll-like receptor (TLR) ligand, and the second inducing agent comprises a molecule with biological activity. In certain embodiments, the TLR ligand comprises a Toll-like receptor 3 (TLR3) ligand. In certain embodiments, the TLR3 ligand comprises poly(I:C). In certain embodiments, the TLR3 ligand comprises poly(A:U). In certain embodiments, the TLR3 ligand is at a concentration from about 10 pg/mL to about 100 µg/mL, from about 100 pg/mL to about 100 µg/mL, from about 1 ng/mL to about 100 µg/mL, from about 5 ng/mL to about 100 µg/mL, from about 10 ng/mL to about 100 µg/mL, from about 100 ng/mL to about 100 µg/mL, from about 0.1 µg/mL to about 50 µg/mL, from about 0.1 µg/mL to about 10 µg/mL, from about 0.25 µg/mL to about 7.5 µg/mL, from about 0.5 µg/mL to about 5 µg/mL, from about 1 µg/mL to about 2.5 µg/mL, or from about 1 µg/mL to about 1.5 µg/mL. In certain embodiments, the TLR3 ligand is present at a concentration of at least 10 pg/mL. In certain embodiments, the TLR3 ligand is present at a concentration of at least 100 pg/mL. In certain embodiments, the TLR3 ligand is present at a concentration of at least 1 ng/mL. In certain embodiments, the TLR3 ligand is present at a concentration of at least 10 ng/mL. In certain embodiments, the TLR3 ligand is present at a concentration of at least 100 ng/mL. In certain embodiments, the TLR3 ligand is present at a concentration of at least 1 µg/mL. In certain embodiments, the TLR3 ligand is present at a concentration of at least 10 µg/mL. In certain embodiments, the TLR3 ligand is present at a concentration of less than 1 g/mL. In certain embodiments, the TLR3 ligand is present at a concentration of less than 100 mg/mL. In certain embodiments, the TLR3 ligand is present at a concentration of less than 10 mg/mL. In certain embodiments, the TLR3 ligand is present at a concentration of less than 1 mg/mL. In certain embodiments, the TLR3 ligand is present at a concentration of less than 500 µg/mL. In certain embodiments, the TLR3 ligand is present at a concentration of less than 200 µg/mL. In certain embodiments, the TLR3 ligand is present at a concentration of less than 100 µg/mL.

Additional Agents

In certain embodiments, disclosed herein, is a medium for producing an immunologically polarized multipotent stem cell population from an unstimulated multipotent stem cell population, the medium comprising a first and a second inducing agent, wherein the first inducing agent comprises a Toll-like receptor (TLR) ligand, and the second inducing agent comprises a molecule with biological activity. In certain embodiments, referring to FIG. 1, the second inducing agent comprises an inhibitor or activator of the TLR signaling pathway. In certain embodiments, the TLR ligand comprises a Toll-like receptor 3 (TLR3) ligand. In certain embodiments, the TLR ligand comprises a Toll-like receptor 4 (TLR4) ligand. In certain embodiments, the second inducing agent comprises a molecule with biological activity. In certain embodiments, the second inducing agent is a different Toll-like receptor ligand from the first inducing agent, a neurotransmitter, a neurotransmitter-like molecule, a small molecule, a polypeptide, or a lipid. In certain embodiments, the second inducing agent is selected from: acetylcholine, alpha-melanocyte-stimulating hormone, melatonin, serotonin, glutamate, norepinephrine, histamine, lipoxinA4, leukotriene B4, and any combination thereof. In certain embodiments, the second inducing agent is histamine. In certain embodiments, the second inducing agent is acetylcholine. In certain embodiments, the second inducing agent is alpha-melanocyte-stimulating hormone. In certain embodiments, the second inducing agent is glutamate. In certain embodiments, the second inducing agent is norepinephrine. In certain embodiments, the second inducing agent is epinephrine. In certain embodiments, the second inducing agent is serotonin. In certain embodiments, the second inducing agent is melatonin. In certain embodiments, the second inducing agent is lipoxin A4. In certain embodiments, the second inducing agent is lipoxin B4. In certain embodiments, the second inducing agent is leukotriene B4. In certain embodiments, the second inducing agent is not erythropoietin. In certain embodiments, the second inducing agent is not a hypoxic condition or a hypoxia mimetic. In certain embodiments, the second inducing agent is not cobalt chloride. In certain embodiments, the second inducing agent is not desferrioxamine. In certain embodiments, histamine, acetylcholine, glutamate, norepinephrine, epinephrine, serotonin, melatonin, lipoxin A4, alpha-melanocyte-stimulating hormone (α-MSH), and leukotriene B4 are all useful in increasing or potentiating MSC2 induction. In certain embodiments, histamine, acetylcholine, glutamate, norepinephrine, epinephrine, serotonin, melatonin, lipoxin A4, alpha-melanocyte-stimulating hormone (α-MSH), and leukotriene B4 are all useful in increasing or potentiating MSC1 induction. In certain embodiments, acetylcholine, glutamate, and lipoxin A4 are useful in increasing or potentiating MSC2 induction. In certain embodiments, serotonin, melatonin, lipoxin A4, and leukotriene B4 are useful in increasing or potentiating MSC1 induction.

Acetylcholine (AcH)

In certain embodiments, the second inducing agent comprises Acetylcholine. In certain embodiments, the concentration of AcH is from about 1 nanomolar to about 100 micromolar. In certain embodiments, the concentration of AcH is at least 1 nanomolar. In certain embodiments, the concentration of AcH is at least 10 nanomolar. In certain embodiments, the concentration of AcH is at least 100 nanomolar. In certain embodiments, the concentration of AcH is at least 1 micromolar. In certain embodiments, the concentration of AcH is at least 10 micromolar. In certain embodiments, the concentration of AcH is less than 100 micromolar. In certain embodiments, the concentration of AcH is less than 10 micromolar. In certain embodiments, the concentration of AcH is less than 1 micromolar. In certain embodiments, the concentration of AcH is less than 100 nanomolar. In certain embodiments, the concentration of AcH is less than 10 nanomolar.

Alpha-Melanocyte-Stimulating Hormone (MSH)

In certain embodiments, the second inducing agent comprises alpha-melanocyte-stimulating hormone (MSH). In certain embodiments, the concentration of MSH is from about 100 picomolar to about 100 nanomolar. In certain embodiments, the concentration of MSH is at least 100 picomolar. In certain embodiments, the concentration of MSH is at least 1 nanomolar. In certain embodiments, the concentration of MSH is at least 10 nanomolar. In certain embodiments, the concentration of MSH is less than 100 nanomolar. In certain embodiments, the concentration of MSH is less than 10 nanomolar. In certain embodiments, the concentration of MSH is less than 1 nanomolar.

Melatonin (MEL)

In certain embodiments, the second inducing agent comprises melatonin (MEL). In certain embodiments, the concentration of MEL is from about 1 nanomolar to about 100 micromolar. In certain embodiments, the concentration of MEL is at least 1 nanomolar. In certain embodiments, the concentration of MEL is at least 10 nanomolar. In certain embodiments, the concentration of MEL is at least 100 nanomolar. In certain embodiments, the concentration of MEL is at least 1 micromolar. In certain embodiments, the concentration of MEL is at least 10 micromolar. In certain embodiments, the concentration of MEL is less than 100 micromolar. In certain embodiments, the concentration of MEL is less than 10 micromolar. In certain embodiments, the concentration of MEL is less than 1 micromolar. In certain embodiments, the concentration of MEL is less than 100 nanomolar. In certain embodiments, the concentration of MEL is less than 10 nanomolar.

Serotonin (5-HT)

In certain embodiments, the second inducing agent comprises serotonin (5-HT). In certain embodiments, the concentration of 5-HT is from about 100 picomolar to about 100 micromolar. In certain embodiments, the concentration of 5-HT is at least 100 picomolar. In certain embodiments, the concentration of 5-HT is at least 1 nanomolar. In certain embodiments, the concentration of MEL is at least 10 nanomolar. In certain embodiments, the concentration of 5-HT is at least 100 nanomolar. In certain embodiments, the concentration of 5-HT is at least 1 micromolar. In certain embodiments, the concentration of 5-HT is at least 10 micromolar. In certain embodiments, the concentration of 5-HT is less than 100 micromolar. In certain embodiments, the concentration of 5-HT is less than 10 micromolar. In certain embodiments, the concentration of 5-HT is less than 1 micromolar. In certain embodiments, the concentration of 5-HT is less than 100 nanomolar. In certain embodiments, the concentration of 5-HT is less than 10 nanomolar. In certain embodiments, the concentration of 5-HT is less than 1 nanomolar.

Glutamate (GLU)

In certain embodiments, the second inducing agent comprises glutamate (GLU). In certain embodiments, the concentration of GLU is from about 10 nanomolar to about 1 millimolar. In certain embodiments, the concentration of GLU is at least 10 nanomolar. In certain embodiments, the concentration of GLU is at least 100 nanomolar. In certain embodiments, the concentration of GLU is at least 1 micromolar. In certain embodiments, the concentration of GLU is at least 10 micromolar. In certain embodiments, the concentration of GLU is at least 100 micromolar. In certain embodiments, the concentration of GLU is less than 1 millimolar. In certain embodiments, the concentration of GLU is less than 100 micromolar. In certain embodiments, the concentration of GLU is less than 10 micromolar. In certain embodiments, the concentration of GLU is less than 1 micromolar. In certain embodiments, the concentration of GLU is less than 100 nanomolar.

Norepinephrine (NEPI)

In certain embodiments, the second inducing agent comprises norepinephrine (NEPI). In certain embodiments, the concentration of NEPI is from about 100 picomolar to about 100 nanomolar. In certain embodiments, the concentration of NEPI is at least 100 picomolar. In certain embodiments, the concentration of NEPI is at least 1 nanomolar. In certain embodiments, the concentration of NEPI is at least 10 nanomolar. In certain embodiments, the concentration of NEPI is less than 100 nanomolar. In certain embodiments, the concentration of NEPI is less than 10 nanomolar. In certain embodiments, the concentration of NEPI is less than 1 nanomolar.

Histamine (HIS)

In certain embodiments, the second inducing agent comprises histamine (HIS). In certain embodiments, the concentration of HIS is from about 10 nanomolar to about 1 millimolar. In certain embodiments, the concentration of HIS is at least 10 nanomolar. In certain embodiments, the concentration of HIS is at least 100 nanomolar. In certain embodiments, the concentration of HIS is at least 1 micromolar. In certain embodiments, the concentration of HIS is at least 10 micromolar. In certain embodiments, the concentration of HIS is at least 100 micromolar. In certain embodiments, the concentration of HIS is less than 1 millimolar. In certain embodiments, the concentration of HIS is less than 100 micromolar. In certain embodiments, the concentration of HIS is less than 10 micromolar. In certain embodiments, the concentration of HIS is less than 1 micromolar. In certain embodiments, the concentration of HIS is less than 100 nanomolar.

Lipoxina4 (Lxa4)

In certain embodiments, the second inducing agent comprises lipoxinA4 (LXA4). In certain embodiments, the concentration of LXA4 is from about 100 picomolar to about 1 millimolar. In certain embodiments, the concentration of LXA4 is at least 100 picomolar. In certain embodiments, the concentration of LXA4 is at least 1 nanomolar. In certain embodiments, the concentration of LXA4 is at least 10 nanomolar. In certain embodiments, the concentration of LXA4 is at least 100 nanomolar. In certain embodiments, the concentration of LXA4 is at least 1 micromolar. In certain embodiments, the concentration of LXA4 is at least 10 micromolar. In certain embodiments, the concentration of LXA4 is at least 100 micromolar. In certain embodiments, the concentration of LXA4 is less than 1 millimolar. In certain embodiments, the concentration of LXA4 is less than 100 micromolar. In certain embodiments, the concentration of LXA4 is less than 10 micromolar. In certain embodiments, the concentration of LXA4 is less than 1 micromolar. In certain embodiments, the concentration of LXA4 is less than 100 nanomolar. In certain embodiments, the concentration of LXA4 is less than 10 nanomolar. In certain embodiments, the concentration of LXA4 is less than 1 nanomolar.

Leukotriene B4 (LTB4)

In certain embodiments, the second inducing agent comprises leukotriene B4 (LTB4). In certain embodiments, the concentration of LTB4 is from about 100 picomolar to about 1 millimolar. In certain embodiments, the concentration of LTB4 is at least 100 picomolar. In certain embodiments, the concentration of LTB4 is at least 1 nanomolar. In certain embodiments, the concentration of LTB4 is at least 10 nanomolar. In certain embodiments, the concentration of LTB4 is at least 100 nanomolar. In certain embodiments, the concentration of LTB4 is at least 1 micromolar. In certain embodiments, the concentration of LTB4 is at least 10 micromolar. In certain embodiments, the concentration of LTB4 is at least 100 micromolar. In certain embodiments, the concentration of LTB4 is less than 1 millimolar. In certain embodiments, the concentration of LTB4 is less than 100 micromolar. In certain embodiments, the concentration of LTB4 is less than 10 micromolar. In certain embodiments, the concentration of LTB4 is less than 1 micromolar. In certain embodiments, the concentration of LTB4 less than 100 nanomolar. In certain embodiments, the concentration of LTB4 is less than 10 nanomolar. In certain embodiments, the concentration of LTB4 is less than 1 nanomolar.

Hypoxia

In certain embodiments, disclosed herein, is a medium for producing an immunologically polarized multipotent stem cell population from an unstimulated multipotent stem cell population, the medium comprising a first and a second inducing agent, wherein the first inducing agent comprises a Toll-like receptor (TLR) ligand, and the second inducing agent comprises a molecule with biological activity. In certain embodiments, the molecule with biological activity comprises a different Toll-like receptor ligand, a neurotransmitter, a neurotransmitter-like molecule, a non-erythropoietin polypeptide, or a lipid. In certain embodiments the molecule with biological activity is selected from the list consisting of histamine, acetylcholine, glutamate, norepinephrine, epinephrine, serotonin, melatonin, lipoxin A4, alpha-melanocyte-stimulating hormone ($\alpha$-MSH), and leukotriene B4. In certain embodiments, the TLR ligand comprises a Toll-like receptor 3 (TLR3) ligand. In certain embodiments, the TLR ligand comprises a Toll-like receptor 4 (TLR4) ligand. In certain embodiments, the second inducing agent is selected from: acetylcholine, alpha-melanocyte-stimulating hormone, melatonin, serotonin, glutamate, norepinephrine, histamine, lipoxinA4, leukotriene B4, and any combination thereof. In certain embodiments, the third inducing agent is a hypoxic condition or a hypoxia mimetic. In certain embodiments, the third inducing agent comprises erythropoietin.

In certain embodiments, the medium described herein comprises a hypoxic condition. In certain embodiments, the hypoxic condition comprises an incubation in a hypoxic or oxygen-depleted environment. In certain embodiments, a hypoxic environment possesses less than 10% oxygen. In certain embodiments, a hypoxic environment possesses less than 8% oxygen. In certain embodiments, a hypoxic environment possesses less than 6% oxygen. In certain embodiments, a hypoxic environment possesses less than 5% oxygen. In certain embodiments, a hypoxic environment possesses less than 4% oxygen. In certain embodiments, a hypoxic environment possesses less than 3% oxygen. In certain embodiments, a hypoxic environment possesses less than 2.5% oxygen. In certain embodiments, a hypoxic environment possesses less than 2.0% oxygen. In certain embodiments, a hypoxic environment possesses less than 1.5% oxygen. In certain embodiments, a hypoxic environment possesses less than 1.0% oxygen. In certain embodiments, a hypoxic environment possesses less than 0.5% oxygen. In certain embodiments, a hypoxic environment possesses effectively 0% oxygen. In certain embodiments, a hypoxic environment possesses from 0.5% to 3.0% oxygen. In certain embodiments, a hypoxic environment possesses from 0.5% to 2.5% oxygen. In certain embodiments, a hypoxic environment possesses from 0.5% to 2.0% oxygen. In certain embodiments, a hypoxic environment possesses from 0.5% to 1.5% oxygen. In certain embodiments, a hypoxic environment possesses from 0.5% to 1.0% oxygen. In certain embodiments, a hypoxic environment possesses from 1.0% to 2.0% oxygen. In certain embodiments, a hypoxic environment possesses from 1.5% to 2.0% oxygen.

In certain embodiments, the medium described herein comprises a hypoxia mimetic. In certain embodiments, the hypoxia mimetic comprises cobalt chloride. In certain embodiments, cobalt chloride is present at a concentration of about 50 µM. In certain embodiments, cobalt chloride is present at a concentration of about 100 µM. In certain embodiments, cobalt chloride is present at a concentration of about 200 µM. In certain embodiments, cobalt chloride is present at a concentration of about 300 µM. In certain embodiments, cobalt chloride is present at a concentration of about 400 µM. In certain embodiments, cobalt chloride is present at a concentration of about 500 µM. In certain embodiments, cobalt chloride is present at a concentration of about 600 µM. In certain embodiments, cobalt chloride is present at a concentration of about 700 µM. In certain embodiments, cobalt chloride is present at a concentration of about 800 µM. In certain embodiments, cobalt chloride is present at a concentration of about 900 µM. In certain embodiments, cobalt chloride is present at a concentration of about 1 mM. In certain embodiments, cobalt chloride is present at a concentration of from about 10 µM to about 1 mM. In certain embodiments, cobalt chloride is present at a concentration of from about 10 µM about 800 µM. In certain embodiments, cobalt chloride is present at a concentration of from about 10 µM to about 500 µM. In certain embodiments, cobalt chloride is present at a concentration of from about 10 µM to about 400 µM. In certain embodiments, cobalt chloride is present at a concentration of from about 10 µM to about 300 µM. In certain embodiments, cobalt chloride is present at a concentration of from about 50 µM to about 300 µM. In certain embodiments, cobalt chloride is present at a concentration of from about 100 µM to about 300 µM. In certain embodiments, cobalt chloride is present at a concentration of from about 150 µM to about 300 µM.

In certain embodiments, the medium described herein comprises a hypoxia mimetic. In certain embodiments, the hypoxia mimetic comprises desferrioxamine. In certain embodiments, desferrioxamine is present at a concentration of about 50 µM. In certain embodiments, desferrioxamine is present at a concentration of about 200 µM. In certain embodiments, desferrioxamine is present at a concentration of about 300 µM. In certain embodiments, desferrioxamine is present at a concentration of about 400 µM. In certain embodiments, desferrioxamine is present at a concentration of about 500 µM. In certain embodiments, desferrioxamine is present at a concentration of about 600 µM. In certain embodiments, desferrioxamine is present at a concentration of about 700 µM. In certain embodiments, desferrioxamine is present at a concentration of about 800 µM. In certain embodiments, desferrioxamine is present at a concentration of about 900 µM. In certain embodiments, desferrioxamine is present at a concentration of about 1 mM. In certain embodiments, desferrioxamine is present at a concentration of from about 10 µM to about 1 mM. In certain embodiments, desferrioxamine is present at a concentration of from about 10 µM about 800 µM. In certain embodiments, desferrioxamine is present at a concentration of from about 10 µM to about 500 µM. In certain embodiments, desferrioxamine is present at a concentration of from about 10 µM to about 400 µM. In certain embodiments, desferrioxamine is present at a concentration of from about 10 µM to about 300 µM. In certain embodiments, desferrioxamine is present at a concentration of from about 50 µM to about 300 µM. In certain embodiments, desferrioxamine is present at a concentration of from about 100 µM to about 300 µM. In certain embodiments, desferrioxamine is present at a concentration of from about 150 µM to about 300 µM.

In certain embodiments, the medium described herein comprises erythropoietin. In certain embodiments, the medium of the invention comprises recombinant erythropoietin. In certain embodiments, the medium of the invention comprises human recombinant erythropoietin. In certain embodiments, the amount of erythropoietin is from about 0.1 ng/mL to about 1.0 mg/mL. In certain embodiments, the amount of erythropoietin is from about 0.1 ng/mL to about 100 ng/mL. In certain embodiments, the amount of erythropoietin is from about 0.1 ng/mL to about 50 ng/mL. In certain embodiments, the amount of erythropoietin is from about 0.1 ng/mL to about 10 ng/mL. In certain embodiments, the amount of erythropoietin is from about 0.1 ng/mL to about 1.0 ng/mL. In certain embodiments, the amount of erythropoietin is from about 0.2 ng/mL to about 0.8 ng/mL. In certain embodiments, the amount of erythropoietin is from about 0.3 ng/mL to about 0.6 ng/mL. In certain embodiments, the amount of erythropoietin is less than 10 mg/mL. In certain embodiments, the amount of erythropoietin is less than 5 mg/mL. In certain embodiments, the amount of erythropoietin is less than 1 mg/mL. In certain embodiments, the amount of erythropoietin is less than 100 ng/mL. In certain embodiments, the amount of erythropoietin is less than 30 ng/mL. In certain embodiments, the amount of erythropoietin is less than 10 ng/mL. In certain embodiments, the amount of erythropoietin is less than 5 ng/mL. In certain embodiments, the amount of erythropoietin is less than 4 ng/mL. In certain embodiments, the amount of erythropoietin is less than 1 ng/mL. In certain embodiments, the amount of erythropoietin is less than 0.8 ng/mL. In certain embodiments, the amount of erythropoietin is less than 1 ng/mL. In certain embodiments, the amount of erythropoietin is less than 5 U/mL. In certain embodiments, the amount of erythropoietin is less than 1 U/mL. In certain embodiments, the amount of erythropoietin is less than 0.5 U/mL. In certain embodiments, the amount of erythropoietin is less than 0.1 U/mL. In certain embodiments, the amount of erythropoietin is less than 0.05 U/mL.

In certain embodiments, disclosed herein, is a medium for producing an immunologically polarized multipotent stem cell population from an unstimulated multipotent stem cell population, the medium comprising a first and a second inducing agent, wherein the first inducing agent comprises a Toll-like receptor (TLR) ligand, and the second inducing agent comprises a molecule with biological activity. In certain embodiments, the TLR ligand comprises a Toll-like receptor 3 (TLR3) ligand. In certain embodiments, the TLR ligand comprises a Toll-like receptor 4 (TLR4) ligand. In certain embodiments, the second inducing agent is selected from: acetylcholine, alpha-melanocyte-stimulating hormone, melatonin, serotonin, glutamate, norepinephrine, histamine, lipoxinA4, leukotriene B4, and any combination thereof. In certain embodiments, the medium comprise a third inducing agent. In certain embodiments, the third inducing agent comprises a hypoxic condition or a hypoxia mimetic. In certain embodiments, the third inducing agent comprises erythropoietin. In certain embodiments, the medium comprise a fourth inducing agent. In certain embodiments, the fourth inducing agent comprises erythropoietin. In certain embodiments, the fourth inducing agent comprises a hypoxic condition or a hypoxia mimetic.

Multipotent Stem Cells

In certain embodiments, disclosed herein, are methods and culture medium for use with multipotent stem cells. In certain embodiments, disclosed herein, are methods and culture medium for use with a multipotent stem cell population. In certain embodiments, the medium comprises one or more multipotent stem cells. In certain embodiments, the medium comprises one or more naïve multipotent stem cells. In certain embodiments, the medium comprises one or more unstimulated multipotent stem cells. In certain embodiments, the medium comprises one or more stimulated multipotent stem cells. In certain embodiments, the multipotent stem cells are of human origin. In certain embodiments, the multipotent stem cells are primary human cells. In certain embodiments, the multipotent stem cells are isolated from blood. In certain embodiments, the multipotent stem cells are isolated from umbilical cord blood. In certain embodiments, the multipotent stem cells are isolated from placenta. In certain embodiments, the multipotent stem cells are isolated from dental pulp. In certain embodiments, the multipotent stem cells are isolated from menstrual blood. In certain embodiments, the multipotent stem cells are isolated from a fetus. In certain embodiments, the multipotent stem cells are isolated from a lipoaspirate. In certain embodiments, the multipotent stem cells are isolated from a biopsy.

Mesenchymal Stem Cells

In certain embodiments, disclosed herein, are methods and culture medium for use with mesenchymal stem cells. In certain embodiments, disclosed herein, are methods and culture medium for use with a mesenchymal stem cell population. In certain embodiments, the medium comprises one or more mesenchymal stem cells. In certain embodiments, the medium comprises one or more naïve mesenchymal stem cells. In certain embodiments, the medium comprises one or more unstimulated mesenchymal stem cells. In certain embodiments, the medium comprises one or more stimulated mesenchymal stem cells. In certain embodiments, the mesenchymal stem cells are of human origin. In certain embodiments, the mesenchymal stem cells are primary human cells. In certain embodiments, the mesenchymal stem cells are isolated from blood. In certain embodiments, the mesenchymal stem cells are isolated from umbilical cord blood. In certain embodiments, the mesenchymal stem cells are isolated from placenta. In certain embodiments, the mesenchymal stem cells are isolated from dental pulp. In certain embodiments, the mesenchymal stem cells are isolated from menstrual blood. In certain embodiments, the mesenchymal stem cells are isolated from a fetus. In certain embodiments, the mesenchymal stem cells are isolated from a lipoaspirate. In certain embodiments, the mesenchymal stem cells are isolated from a biopsy.

Type 1 Polarized Multipotent Stem Cells

In certain embodiments, disclosed herein, are methods to induce immunological polarization in multipotent or mesenchymal stem cells. In certain embodiments, disclosed herein, are media to induce immunological polarization in multipotent stem cells. In certain embodiments, disclosed herein, are polarized multipotent stem cells. In certain embodiments, the cells exhibit type 1 polarization. Type 1 polarization is marked by expression or release of pro-inflammatory mediators. Cells treated with TLR4 ligands will exhibit Type 1 polarization. Type 1 polarization is marked by expression of TNFSF10 (TRAIL). In certain embodiments, the methods and culture medium of this disclosure induce expression of TNFSF10. In certain embodiments, the methods and culture medium of this disclosure induce expression of TNFSF10 by 2-fold compared to unstimulated cells. In certain embodiments, the methods and culture medium of this disclosure induce expression of TNFSF10 by 5-fold compared to unstimulated cells. In certain embodiments, the methods and culture medium of this disclosure induce expression of TNFSF10 by 10-fold compared to unstimulated cells. In certain embodiments, the methods and culture medium of this disclosure induce expression of TNFSF10 by 50-fold compared to unstimulated cells. In certain embodiments, the methods and culture medium of this disclosure induce expression of TNFSF10 by 100-fold compared to unstimulated cells. In certain embodiments, the methods and culture medium of this disclosure induce expression of TNFSF10 by 200-fold compared to unstimulated cells. In certain embodiments, the methods and culture medium of this disclosure induce expression of TNFSF10 by 500-fold compared to unstimulated cells. In certain embodiments, the methods and culture medium of this disclosure induce expression of TNFSF10 by 1,000-fold compared to unstimulated cells. In certain embodiments, the methods and culture medium of this disclosure induce expression of TNFSF10 by 10,000-fold compared to unstimulated cells.

In certain embodiments, disclosed herein, are type 1 polarized multipotent or mesenchymal stem cells. In certain embodiments, the type 1 polarized multipotent stem cells express TNFSF10. In certain embodiments, the type 1 polarized multipotent stem cells express 2-fold more TNFSF10 compared to unstimulated cells. In certain embodiments, the type 1 polarized multipotent stem cells express 5-fold more TNFSF10 compared to unstimulated cells. In certain embodiments, the type 1 polarized multipotent stem cells express 10-fold more TNFSF10 compared unstimulated cells. In certain embodiments, the type 1 polarized multipotent stem cells express 50-fold more TNFSF10 compared to unstimulated cells. In certain embodiments, the type 1 polarized multipotent stem cells express 100-fold more TNFSF10 compared to unstimulated cells. In certain embodiments, the type 1 polarized multipotent stem cells express 500-fold more TNFSF10 compared to unstimulated cells. In certain embodiments, the type 1 polarized multipotent stem cells express 1,000-fold more TNFSF10 compared to unstimulated cells. In certain embodiments, the type 1 polarized multipotent stem cells express 10,000-fold more TNFSF10 compared to unstimulated cells.

In certain embodiments, disclosed herein, are type 1 polarized multipotent or mesenchymal stem cells. In certain embodiments, the type 1 polarized multipotent stem cells express elevated levels of certain miRNAs compared to unstimulated multipotent stem cells. In certain embodiments, the elevated miRNAs comprise any one or more of miR-146, miR-155, miR-1305, miR-575, and miR-1973. In certain embodiments, the elevated miRNAs comprise any one, two, three, four, or all five of miR-146, miR-155, miR-1305, miR-575, and miR-1973. The levels of any one of these miRNAs can be elevated by at least about 2-fold, 3-fold, 4-fold, 5-fold or more compared to an unstimulated multipotent stem cell population. In certain embodiments, the type 1 polarized multipotent stem cells express reduced levels of certain miRNAs compared to unstimulated multipotent stem cells. In certain embodiments, the reduced miRNAs comprise miRNA-24-3p. The levels of this miRNA can be reduced by at least about 2-fold, 3-fold, 4-fold, 5-fold, or more compared to an unstimulated multipotent sell population.

Type 2 Polarized Multi Potent Stem Cells

In certain embodiments, disclosed herein, are methods to induce immunological type 2 polarization in multipotent or mesenchymal stem cells. In certain embodiments, disclosed herein, are media to induce type 2 polarization in multipotent stem cells. Type 2 polarization is marked by expression or release of anti-inflammatory mediators. Cells treated with TLR3 ligands will exhibit type 2 polarization. Type 2 polarization is marked by expression of CXCL9. In certain embodiments, the methods and culture medium of this disclosure induce expression of CXCL9. In certain embodiments, the methods and culture medium of this disclosure induce expression of CXCL9 by 2-fold compared to unstimulated cells. In certain embodiments, the methods and culture medium of this disclosure induce expression of CXCL9 by 5-fold compared to unstimulated cells. In certain embodiments, the methods and culture medium of this disclosure induce expression of CXCL9 by 10-fold compared to unstimulated cells. In certain embodiments, the methods and culture medium of this disclosure induce expression of CXCL9 by 50-fold compared to unstimulated cells. In certain embodiments, the methods and culture medium of this disclosure induce expression of CXCL9 by 100-fold compared to unstimulated cells. In certain embodiments, the methods and culture medium of this disclosure induce expression of CXCL9 by 200-fold compared to unstimulated cells. In certain embodiments, the methods and culture medium of this disclosure induce expression of CXCL9 by 500-fold compared to unstimulated cells.

In certain embodiments, disclosed herein, are type 2 polarized multipotent or mesenchymal stem cells. In certain embodiments, the type 2 polarized multipotent stem cells express CXCL9. In certain embodiments, the type 2 polarized multipotent stem cells express 2-fold more CXCL9 compared to unstimulated cells. In certain embodiments, the type 2 polarized multipotent stem cells express 5-fold more CXCL9 compared to unstimulated cells. In certain embodiments, the type 2 polarized multipotent stem cells express 10-fold more CXCL9 compared to unstimulated cells. In certain embodiments, the type 2 polarized multipotent stem cells express 50-fold more CXCL9 compared to unstimulated cells. In certain embodiments, the type 2 polarized multipotent stem cells express 100-fold more CXCL9 compared to unstimulated cells. In certain embodiments, the type 2 polarized multipotent stem cells express 200-fold more CXCL9 compared to unstimulated cells. In certain embodiments, the type 2 polarized multipotent stem cells express 500-fold more CXCL9 compared to unstimulated cells.

In certain embodiments, disclosed herein, the type 2 polarized multipotent or mesenchymal stem cells express of any of the following genes by at least 2-fold when compared to an unstimulated cell population: CXCL9; EGFR; IRF1; A2M; FAS; IL2RG; MMP3; GBP1; ISG15; FCGR1; NFKB1; NOS2A; USF1; YY1; JAK2; STA2; STAT4; STAT5; SOCS1; or IRF1. In certain embodiments, the type 2 polarized multipotent stem cells express any of the following genes by at least 2-fold when compared to an unstimulated cell population: EPOR; F2R; STAM; PDGFRA; PIAS2; MYC; SH2B1; or CSF2RB. In certain embodiments, the type 2 polarized multipotent stem cells express any of the following genes by at least 10-fold when compared to an unstimulated cell population: CXCL9; GBP1; ISG15; SOCS1; MMP3; JAK2 or IRF1. In certain embodiments, the type 2 polarized multipotent stem cells express of any of the following genes by at least 20-fold when compared to an unstimulated cell population: CXCL9; GBP1; ISG15; or SOCS1.

In certain embodiments, disclosed herein, are type 2 polarized multipotent or mesenchymal stem cells. In certain embodiments, the type 2 polarized multipotent stem cells express elevated levels of certain miRNAs compared to unstimulated multipotent stem cells. In certain embodiments, the elevated miRNAs comprise any one or more of miR-Let 7a/d, miR-17_1, miR-222, miR-92a, and miR-1260a. In certain embodiments, the elevated miRNAs comprise any one, two, three, four, or all five of miR-Let 7a/d, miR-17_1, miR-222, miR-92a, or miR-1260a. The levels of any one of these miRNAs can be elevated by at least about 2-fold, 3-fold, 4-fold, 5-fold, or more compared to an unstimulated multipotent sell population. In certain embodiments, the type 2 polarized multipotent stem cells express reduced levels of certain miRNAs compared to unstimulated multipotent stem cells. In certain embodiments, the reduced miRNAs comprise miRNA-222. The levels of this miRNA can be reduced by at least about 2-fold, 3-fold, 4-fold, 5-fold, or more compared to an unstimulated multipotent sell population.

Cell Uniformity

In certain embodiments, the methods and culture medium of the current disclosure allow for increased uniformity of polarized multipotent cells after culture. In some embodiments, greater than 60% of cells express a type 1 marker. In some embodiments, greater than 70% of cells express a type 1 marker. In some embodiments, greater than 80% of cells express a type 1 marker. In some embodiments, greater than 90% of cells express a type 1 marker. In some embodiments, greater than 95% of cells express a type 1 marker. In some embodiments, greater than 98% of cells express a type 1 marker. In certain embodiments, the type 1 marker is TNFSF10. The marker can be measured by any suitable method, for example, immunohistochemistry, ELISA, flow cytometry, western blot, qRT-PCR, northern blot, or digital PCR.

In certain embodiments, the methods and culture medium of the current disclosure allow for increased uniformity of polarized multipotent cells after culture. In some embodiments, greater than 60% of cells express a type 2 marker. In some embodiments, greater than 70% of cells express a type 2 marker. In some embodiments, greater than 80% of cells express a type 2 marker. In some embodiments, greater than 90% of cells express a type 2 marker. In some embodiments, greater than 95% of cells express a type 2 marker. In some embodiments, greater than 98% of cells express a type 2 marker. In certain embodiments, the type 2 marker is CXCL9. The marker can be measured by any suitable method, for example, immunohistochemistry, ELISA, flow cytometry, western blot, qRT-PCR, northern blot, or digital PCR.

Methods

In certain embodiments, the methods described herein provide for a certain amount of contact between the culture media and the multipotent stem cell. In certain embodiments, the multipotent cells are in contact with the medium or inducing agents of this disclosure for less than 24 hours. In certain embodiments, the multipotent cells are in contact with the medium or inducing agents of this disclosure for less than 8 hours. In certain embodiments, the multipotent cells are in contact with the medium or inducing agents of this disclosure for less than 4 hours. In certain embodiments, the multipotent cells are in contact with the medium or inducing agents of this disclosure for less than 2 hours. In certain embodiments, the multipotent cells are in contact with the medium or inducing agents of this disclosure for less than 1 hour. In certain embodiments, the multipotent cells are in contact with the medium or inducing agents of this disclosure for greater than 1 minute. In certain embodiments, the multipotent cells are in contact with the medium or inducing agents of this disclosure for greater than 1 hour. In certain embodiments, the multipotent cells are in contact with the medium or inducing agents of this disclosure for greater than 2 hours. In certain embodiments, the multipotent cells are in contact with the medium or inducing agents of this disclosure for greater than 4 hours. In certain embodiments, the multipotent cells are in contact with the medium or inducing agents of this disclosure for greater than 8 hours.

Secreted Pro-Inflammatory Factors

In certain embodiments, the methods and culture media described herein cause stimulated multipotent stem cells to secrete factors that are therapeutically useful. In certain embodiments, the factor is secreted by a mesenchymal stem cell. In certain embodiments, the factor is pro-inflammatory. In certain embodiments, the factor is secreted in response to stimulation with a TLR4 ligand. In certain embodiments, the TLR4 ligand comprises LPS or aminoalkyl glucosaminide. In certain embodiments, the factor is secreted in response to stimulation with a TLR4 ligand and erythropoietin and a hypoxic condition. In certain embodiments, the factor is secreted in response to stimulation with a TLR4 ligand and erythropoietin and a hypoxic condition and an additional inducing agent selected from: acetylcholine, alpha-melanocyte-stimulating hormone, melatonin, serotonin, glutamate, norepinephrine, histamine, lipoxinA4, leukotriene B4, and any combination thereof. In certain embodiments, the secreted factor is a cytokine. In certain embodiments, the factor is secreted in response to stimulation with a TLR4 ligand and an additional inducing agent selected from: acetylcholine, alpha-melanocyte-stimulating hormone, melatonin, serotonin, glutamate, norepinephrine, histamine, lipoxinA4, leukotriene B4, and any combination thereof. In certain embodiments, the cytokine comprises IL-3. In certain embodiments, the cytokine comprises IL-6. In certain embodiments, the cytokine comprises IL-8. In certain embodiments, the cytokine comprises IL-17. In certain embodiments, the cytokine comprises interferon beta. In certain embodiments, the secreted factor comprises a chemokine. In certain embodiments, the chemokine comprises LIF. In certain embodiments, the chemokine comprises GM-CSF. In certain embodiments, the chemokine comprises MIG. In certain embodiments, the chemokine comprises MCP-1. In certain embodiments, the chemokine comprises TRAIL. In certain embodiments, the secreted factor comprises an miRNA. In certain embodiments, the miRNA comprises miR-146. In certain embodiments, the miRNA comprises miR-155. In certain embodiments, the secreted factor comprises a combination of a cytokine, chemokine, or miRNA. In certain embodiments, the secreted factor is not isolated from the stimulated cell culture medium and present along with all the rest in a conditioned media that can be used to treat a subject or contact a cell population that is administered to a subject.

Secreted Anti-Inflammatory Factors

In certain embodiments, the methods and culture media described herein cause stimulated multipotent stem cells to secrete factors that are therapeutically useful. In certain embodiments, the factor is secreted by a mesenchymal stem cell. In certain embodiments, the factor is anti-inflammatory. In certain embodiments, the factor is secreted in response to stimulation with a TLR3 ligand. In certain embodiments, the TLR3 ligand comprises poly(I:C) or poly(A:U). In certain embodiments, the factor is secreted in response to stimulation with a TLR3 ligand, erythropoietin, and a hypoxic condition. In certain embodiments, the factor is secreted in response to stimulation with a TLR3 ligand, erythropoietin, a hypoxic condition, and an additional inducing agent selected from: acetylcholine, alpha-melanocyte-stimulating hormone, melatonin, serotonin, glutamate, norepinephrine, histamine, lipoxinA4, leukotriene B4, and any combination thereof. In certain embodiments, the secreted factor is a cytokine. In certain embodiments, the factor is secreted in response to stimulation with a TLR3 ligand an additional inducing agent selected from: acetylcholine, alpha-melanocyte stimulating hormone, melatonin, serotonin, glutamate, norepinephrine, histamine, lipoxinA4, leukotriene B4, and any combination thereof. In certain embodiments, the secreted factor is a cytokine. In certain embodiments, the cytokine comprises IL-4. In certain embodiments, the cytokine comprises IL-10. In certain embodiments, the cytokine comprises IL-13. In certain embodiments, the cytokine comprises TGF beta. In certain embodiments, the secreted factor comprises a chemokine. In certain embodiments, the chemokine comprises CXCL9. In certain embodiments, the chemokine comprises CCL5. In certain embodiments, the chemokine comprises CXCL10. In certain embodiments, the secreted factor comprises an miRNA. In certain embodiments, the miRNA comprises miR Let7a/d. In certain embodiments, the miRNA comprises miR-17/92a. In certain embodiments, the secreted factor comprises a combination of a cytokine, chemokine, or miRNA. In certain embodiments, the secreted factor comprises prostaglandin E2. In certain embodiments, the secreted factor comprises indoleamine 2,3-dioxygenase. In certain embodiments, the secreted factor is not isolated from the stimulated cell culture medium and present along with all the rest in a conditioned media that can be used to treat a subject or contact a cell population that is administered to a subject.

Isolation of Secreted Factors

In certain embodiments, the secreted factors described herein are isolated from culture media that has been in contact with a stimulated multipotent stem cell population of the current disclosure. In certain embodiments, the secreted factors described herein are isolated from culture media that has been in contact with a stimulated mesenchymal stem cell population of the current disclosure. In certain embodiments, the culture medium has been in contact with the stimulated cell population for greater than 1 hour. In certain embodiments, the culture medium has been in contact with the stimulated cell population for greater than 2 hours. In certain embodiments, the culture medium has been in contact with the stimulated cell population for greater than 4 hours. In certain embodiments, the culture medium has been in contact with the stimulated cell population for greater than 8 hours. In certain embodiments, the stem cell population has been in contact with the culture medium for greater than 24 hours. In certain embodiments, the secreted factor is isolated from the culture media by any suitable method including, but not limited to, filtering, centrifugation, precipitation, chromatography, and freezing. In certain embodiments, the secreted factors are not isolated from the culture media.

Secreted Pro-Inflammatory Extracellular Vesicles

Extracellular vesicles are cell-derived vesicles that are present in many and perhaps all eukaryotic fluids, including blood, urine, and conditioned medium of cell cultures. These extracellular vesicles are derived from cellular endosomal and plasma membranes, and can contain DNAs, RNAs (including miRNAs), proteins, polypeptides, lipids, and small molecules. Extracellular vesicles are cell-derived small vesicles and include exosomes, microvesicles, and apoptotic bodies. In certain embodiments, the extracellular vesicles comprise exosomes. In certain embodiments, the methods and culture mediums described herein cause stimulated multipotent stem cells to secrete extracellular vesicles that are therapeutically useful. In certain embodiments, the extracellular vesicle is secreted by a mesenchymal stem cell. In certain embodiments, the extracellular vesicle is pro-inflammatory. In certain embodiments, the extracellular vesicle is secreted in response to stimulation with a TLR4 ligand. In certain embodiments, the TLR4 ligand comprises LPS or aminoalkyl glucosaminide. In certain embodiments, the extracellular vesicle is secreted in response to stimulation with a TLR4 ligand, erythropoietin, and a hypoxic condition. In certain embodiments, the extracellular vesicle is secreted in response to stimulation with a TLR4 ligand, erythropoietin, a hypoxic condition, and an additional inducing agent selected from: acetylcholine, alpha-melanocyte-stimulating hormone, melatonin, serotonin, glutamate, norepinephrine, histamine, lipoxinA4, leukotriene B4, and any combination thereof. In certain embodiments, the extracellular vesicle is secreted in response to stimulation with a TLR4 ligand and an additional inducing agent selected from: acetylcholine, alpha-melanocyte-stimulating hormone, melatonin, serotonin, glutamate, norepinephrine, histamine, lipoxinA4, leukotriene B4, and any combination thereof. In certain embodiments, the extracellular vesicle comprises a cytokine. In certain embodiments, the extracellular vesicle comprises IL-3. In certain embodiments, the extracellular vesicle comprises IL-6. In certain embodiments, the extracellular vesicle comprises IL-8. In certain embodiments, the extracellular vesicle comprises IL-17. In certain embodiments, the extracellular vesicle comprises interferon beta. In certain embodiments, the extracellular vesicle comprises a chemokine. In certain embodiments, the extracellular vesicle comprises LIF. In certain embodiments, the extracellular vesicle comprises GM-CSF. In certain embodiments, the extracellular vesicle comprises MIG. In certain embodiments, the extracellular vesicle comprises MCP-1. In certain embodiments, the chemokine comprises TRAIL. In certain embodiments, the extracellular vesicle comprises an miRNA. In certain embodiments, the extracellular vesicle comprises miR-146. In certain embodiments, the extracellular vesicle comprises miR-155. In certain embodiments, the extracellular vesicle comprises a combination of a cytokine, chemokine, or miRNA. In a certain embodiment, the pro-inflammatory extracellular vesicle comprises one or more proteins that are elevated compared to extracellular vesicles secreted from a non-stimulated naïve multipotent cell population. In certain embodiments, the one or more proteins comprise an elevated level of any one or more of glyceraldehyde-3-phosphate dehydrogenase (GAPDH), junction plakoglobin (JUP), desmoplakin (DSP), moesin (MSN), vimentin (VIM), actin (ACTB), or annexin A2 (ANXA2) compared to an extracellular vesicle from a naïve unstimulated multipotent stem cell. In certain embodiments, the extracellular vesicle comprises an elevated level of any two, three, four, five, six, or all seven of glyceraldehyde-3-phosphate dehydrogenase (GAPDH), junction plakoglobin (JUP), desmoplakin (DSP), moesin (MSN), vimentin (VIM), actin (ACTB), or annexin A2 (ANXA2) compared to an extracellular vesicle from a naïve unstimulated multipotent stem cell. In certain embodiments, any of these proteins can be elevated by 2-fold, 3-fold, 5-fold, 10-fold, 15-fold, 20-fold, or more compared to an unstimulated multipotent cell. In a certain embodiment, the pro-inflammatory extracellular vesicle comprises one or more proteins that are reduced compared to extracellular vesicles secreted from a non-stimulated naïve multipotent cell population. In certain embodiments, the one or more proteins comprise a reduced level of any one or more of thrombospondin-1 (THBS1), collagen alpha-2 (VI) chain (COL6A2), decorin (DCN), insulin-like growth factor-binding protein 7 (IGFBP7), lysyl oxidase homolog 2 (LOXL2), biglycan (BGN), or collagen alpha-3(VI) chain (COL6A3). In certain embodiments, the extracellular vesicle comprises a reduced level of any two, three, four, five, six, or all seven of thrombospondin-1 (THBS1), collagen alpha-2 (VI) chain (COL6A2), decorin (DCN), insulin-like growth factor-binding protein 7 (IGFBP7), lysyl oxidase homolog 2 (LOXL2), biglycan (BGN), or collagen alpha-3(VI) chain (COL6A3). In certain embodiments, any of these proteins can be reduced by 2-fold, 3-fold, 5-fold, 10-fold, or more compared to an unstimulated multipotent cell.

Secreted Anti-Inflammatory Extracellular Vesicles

In certain embodiments, the methods and culture media described herein cause stimulated multipotent stem cells to secrete extracellular vesicles that are therapeutically useful. In certain embodiments, the extracellular vesicle is secreted by a mesenchymal stem cell. In certain embodiments, the extracellular vesicle is anti-inflammatory. In certain embodiments, the extracellular vesicle is secreted in response to stimulation with a TLR3 ligand. In certain embodiments, the TLR3 ligand comprises poly(I:C) or poly(A:U). In certain embodiments, the extracellular vesicle is secreted in response to stimulation with a TLR3 ligand, erythropoietin, and a hypoxic condition. In certain embodiments, the extracellular vesicle is secreted in response to stimulation with a TLR3 ligand, erythropoietin, a hypoxic condition, and an additional inducing agent selected from: acetylcholine, alpha-melanocyte-stimulating hormone, melatonin, serotonin, glutamate, norepinephrine, histamine, lipoxinA4, leukotriene B4, and any combination thereof. In certain embodiments, the extracellular vesicle comprises a cytokine. In certain embodiments, the extracellular vesicle is secreted in response to stimulation with a TLR3 ligand and an additional inducing agent selected from: acetylcholine, alpha-melanocyte-stimulating hormone, serotonin, glutamate, norepinephrine, histamine, lipoxinA4, leukotriene B4, and any combination thereof. In certain embodiments, the extracellular vesicle comprises a cytokine. In certain embodiments, the extracellular vesicle comprises IL-4. In certain embodiments, the extracellular vesicle comprises IL-10. In certain embodiments, the extracellular vesicle comprises IL-13. In certain embodiments, the extracellular vesicle comprises TGF beta. In certain embodiments, the extracellular vesicle comprises a chemokine. In certain embodiments, the extracellular vesicle comprises CXCL9. In certain embodiments, the extracellular vesicle comprises CCL5. In certain embodiments, the extracellular vesicle comprises CXCL10. In certain embodiments, the extracellular vesicle comprises an miRNA. In certain embodiments, the extracellular vesicle comprises miR Let7a/d. In certain embodiments, the extracellular vesicle comprises miR-17/92a. In certain embodiments, the extracellular vesicle comprises a combination of a cytokine, chemokine, or miRNA. In certain embodiments, the extracellular vesicle comprises prostaglandin E2. In certain embodiments, the extracellular vesicle comprises indoleamine 2,3-dioxygenase. In a certain embodiment, the anti-inflammatory extracellular vesicle comprises one or more proteins that are elevated compared to extracellular vesicles secreted from a non-stimulated multipotent cell population. In certain embodiments, the one or more proteins comprise an elevated level of any one or more of myosin-1 (MYH1), myosin-2 (MTH2), myosin-7 (MYH-7), or tissue factor pathway inhibitor 2 (TFPI2), compared to an extracellular vesicle from a naïve unstimulated multipotent stem cell. In certain embodiments, the extracellular vesicle comprises an elevated level of any two, three, or all four of myosin-1 (MYH1), myosin-2 (MTH2), myosin-7 (MYH-7), or tissue factor pathway inhibitor 2 (TFPI2) compared to an extracellular vesicle from a naïve unstimulated multipotent stem cell. In certain embodiments, any of these proteins can be elevated by 2-fold, 3-fold, 5-fold, 10-fold, 15-fold, 20-fold or more compared to an unstimulated multipotent cell. In a certain embodiment, the anti-inflammatory extracellular vesicle comprises one or more proteins that are reduced compared to extracellular vesicles secreted from a naïve non-stimulated multipotent cell population. In certain embodiments, the one or more proteins comprise a reduced level of any one or more of collagen alpha-1(I) chain (COL6A3), sulfhydryl oxidase 1 (QSOX1), decorin-7 (DCN), collagen alpha-2(VI) chain (COL6A2), Thrombospondin-1 (THBS1), or collagen alpha-1(I) chain (COL1A1) compared to an extracellular vesicle from a naïve unstimulated multipotent stem cell. In certain embodiments, the extracellular vesicle comprises a reduced level of any two, three, four, five or all six of collagen alpha-1(I) chain (COL6A3), sulfhydryl oxidase 1 (QSOX1), decorin-7 (DCN), collagen alpha-2(VI) chain (COL6A2), Thrombospondin-1 (THBS1), or collagen alpha-1(I) chain (COL1A1) compared to an extracellular vesicle from a naïve unstimulated multipotent stem cell. In certain embodiments, any of these proteins can be reduced by 2-fold, 3-fold, 5-fold, 10-fold, or more compared to an unstimulated multipotent cell.

Isolation of Extracellular Vesicles

In certain embodiments, the extracellular vesicles described herein are isolated from culture media that has been in contact with a stimulated multipotent stem cell population of the current disclosure. In certain embodiments, the extracellular vesicles described herein are isolated from culture media that has been in contact with a stimulated mesenchymal stem cell population of the current disclosure. In certain embodiments, the culture medium has been in contact with the stimulated cell population for greater than 1 hour. In certain embodiments, the culture medium has been in contact with the stimulated cell population for greater than 2 hours. In certain embodiments, the culture medium has been in contact with the stimulated cell population for greater than 4 hours. In certain embodiments, the culture medium has been in contact with the stimulated cell population for greater than 8 hours. In certain embodiments, the culture medium has been in contact with the stimulated cell population for greater than 24 hours. The extracellular vesicles can be isolated and/or purified from the culture media. Suitable methods for isolating extracellular vesicles from a culture medium are known in the art. In certain embodiments, the extracellular vesicles are isolated from the culture media by any suitable method including, but not limited to, filtering, centrifugation, ultracentrifugation, density gradient separation, precipitation, immunoaffinty separation, chromatography, and freezing. In certain embodiments, the extracellular vesicles are not isolated from the culture media.

Therapeutic Methods

In certain embodiments, described herein, the methods, culture media, cells, secreted factors, and extracellular vesicles are useful therapeutically. For example FIG. 2 depicts a flow chart of a non-limiting treatment protocol of the methods, culture media, cells, secreted factors, and extracellular vesicles described herein. In certain embodiments, the methods, culture media, cells, secreted factors, and extracellular vesicles described herein are useful for treating cancer. In certain embodiments, the methods, culture media, cells, secreted factors, and extracellular vesicles described herein are useful for treating autoimmune diseases. In certain embodiments, the methods, culture media, cells, secreted factors, and extracellular vesicles described herein are useful for treating inflammatory diseases. In certain embodiments, multipotent stem cells treated with medium comprising TLR4 ligand are useful for treating cancer. In certain embodiments, multipotent stem cells treated with medium comprising TLR3 ligand are useful for treating autoimmune or inflammatory disease. In certain embodiments, mesenchymal stem cells treated with medium comprising TLR4 ligand are useful for treating cancer. In certain embodiments, mesenchymal stem cells treated with medium comprising TLR3 ligand are useful for treating autoimmune or inflammatory disease.

In certain embodiments, multipotent stem cells treated with methods comprising contacting the multipotent stem cell with TLR4 ligand are useful for treating cancer. In certain embodiments, multipotent stem cells treated with methods comprising contacting the multipotent stem cell with a TLR3 ligand are useful for treating autoimmune or inflammatory diseases. In certain embodiments, mesenchymal stem cells treated with methods comprising contacting the mesenchymal stem cell with TLR4 ligand are useful for treating cancer. In certain embodiments, mesenchymal stem cells treated with methods comprising contacting the mesenchymal stem cell with TLR3 ligand are useful for treating autoimmune or inflammatory diseases.

In certain embodiments, multipotent stem cells treated with medium comprising TLR4 ligand are useful for treating cancer. In certain embodiments, factors or extracellular vesicles secreted from multipotent stem cells treated with medium comprising TLR4 ligand are useful for treating cancer. In certain embodiments, mesenchymal stem cells treated with medium comprising TLR3 ligand are useful for treating autoimmune or inflammatory disease. In certain embodiments, factors or extracellular vesicles secreted from mesenchymal stem cells treated with medium comprising TLR3 ligand are useful for treating autoimmune or inflammatory disease.

In certain embodiments, extracellular vesicles or factors secreted from multipotent stem cells treated with methods comprising contacting the multipotent stem cell with TLR4 ligand are useful for treating cancer. In certain embodiments, extracellular vesicles or factors secreted from multipotent stem cells treated with methods comprising contacting the multipotent stem cell with TLR3 ligand are useful for treating autoimmune or inflammatory diseases. In certain embodiments, extracellular vesicles or factors secreted from mesenchymal stem cells treated with methods comprising contacting the mesenchymal stem cell with TLR4 ligand are useful for treating cancer. In certain embodiments, extracellular vesicles or factors secreted from mesenchymal stem cells treated with methods comprising contacting the mesenchymal stem cell with TLR3 ligand are useful for treating autoimmune or inflammatory diseases.

This disclosure provides a method of cellular therapy comprising: (a) providing a population of multipotent stem cells; (b) contacting the stem cell population with any of the media described herein; (c) culturing the cells under appropriate conditions; and (d) administering the stimulated cells to a subject. In certain embodiments, the disclosure provides a method of cellular therapy comprising: (a) providing a population of mesenchymal stem cells; (b) contacting the stem cell population with any of the media described herein; (c) culturing the cells under appropriate conditions; and (d) administering the stimulated cells to a subject. In a certain embodiment, the cell population is harvested from a vessel that comprises both cells and medium by a step comprising removal from the vessel, centrifugation, ultracentrifugation, filtration, dialysis, washing, and suspension in an appropriate diluent such as sterile neutral buffered saline.

Autoimmune and Inflammatory Diseases

In certain embodiments, the methods, cells, culture medium, extracellular vesicles, and secreted factors of this disclosure are for the treatment of autoimmune diseases. In certain embodiments, the methods, cells, culture medium, extracellular vesicles, and secreted factors of this disclosure are for the treatment of acute optic neuritis, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, bronchiolitis obliterans, cardiomyopathy, celiac sprue-dermatitis, chronic fatigue immune dysfunction syndrome (CF1DS), chronic inflammatory demyelinating polyneuropathy, Churg-Strauss syndrome, cicatrical pemphigoid, CREST syndrome, cold agglutinin disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomenon, Reiter's syndrome, sarcoidosis, scleroderma, progressive systemic sclerosis, Sjogren's syndrome, Good pasture's syndrome, stiff-man syndrome, systemic lupus erythematosus, lupus erythematosus, takayasu arteritis, temporal arteritis/giant cell arteritis, ulcerative colitis, uveitis, vasculitides such as dermatitis herpetiformis vasculitis, vitiligo, Wegner's granulomatosis, Anti-Glomerular Basement Membrane Disease, Antiphospholipid Syndrome, Autoimmune Diseases of the Nervous System, Familial Mediterranean Fever, Lambert-Eaton Myasthenic Syndrome, Sympathetic Ophthalmia, Polyendocrinopathies, or Psoriasis.

In certain embodiments, the methods, cells, culture medium, extracellular vesicles, and secreted factors of this disclosure are for the treatment of an inflammatory disorder. In certain embodiments, the inflammatory disorder is Crohn's disease, type 1 diabetes mellitus, rheumatoid arthritis, inflammatory bowel disease, psoriasis, psoriatic arthritis, ankylosing spondylitis, systemic lupus erythematosus, Hashimoto's disease, graft-versus-host disease, Sjogren's syndrome, pernicious anemia, Addison disease, scleroderma, Goodpasture's syndrome, ulcerative colitis, autoimmune hemolytic anemia, sterility, myasthenia gravis, multiple sclerosis, Basedow's disease, thrombopenia purpura, Guillain-Barre syndrome, allergy, asthma, atopic disease, arteriosclerosis, myocarditis, cardiomyopathy, glomerular nephritis, hypoplastic anemia, and rejection after organ transplantation. In certain embodiments, the inflammatory disorder is Acute optic neuritis, diabetic neuropathy, Krabbe Disease, acute lung injury, Crohn's Disease Celiac Disease, rheumatoid arthritis (RA), Inflammatory Bowel Disease (IBD), asthma, encephalitis, chronic obstructive pulmonary disease (COPD), inflammatory osteolysis, allergic disorders, septic shock, pulmonary fibrosis (e.g., idiopathic pulmonary fibrosis), inflammatory vacultides (e.g., polyarteritis nodosa, Wegner's granulomatosis, Takayasu's arteritis, temporal arteritis, and lymphomatoid granulomatosis), post-traumatic vascular angioplasty (e.g., restenosis after angioplasty), undifferentiated spondyloarthropathy, undifferentiated arthropathy, arthritis, inflammatory osteolysis, chronic hepatitis, or chronic inflammation resulting from chronic viral or bacterial infections.

Cancer

In certain embodiments, the methods, cells, culture medium, extracellular vesicles, and secreted factors of this disclosure are for the treatment of cancer. In certain embodiments, the methods, cells, culture medium, extracellular vesicles, and secreted factors of this disclosure are for the treatment of tumors. In certain embodiments, the methods, cells, culture medium, extracellular vesicles, and secreted factors of this disclosure are for augmenting the treatment of cancer. In certain embodiments, the cancer is Acute Lymphoblastic Leukemia, Adult; Acute Lymphoblastic Leukemia, Childhood; Acute Myeloid Leukemia, Adult; Acute Myeloid Leukemia, Childhood; Adreno cortical Carcinoma; AIDS-Related Cancers; AIDS-Related Lymphoma; Anal Cancer; Appendix Cancer; Astrocytomas; Atypical Teratoid/Rhabdoid Tumor; Basal Cell Carcinoma; Bile Duct Cancer, Extrahepatic; Bladder Cancer; Bone Cancer, Osteosarcoma and Malignant Fibrous Histiocytoma; Brain Stem Glioma; Brain Tumor; Central Nervous System Embryonal Tumors; Astrocytomas; Craniopharyngioma; Ependymoblastoma; Brain Tumor, Ependymoma; Medulloblastoma; Medulloepithelioma; Pineal Parenchymal Tumors of Intermediate Differentiation; Supratentorial Primitive Neuro ectodermal Tumors and Pineoblastoma; Brain and Spinal Cord Tumors; Breast Cancer; Breast Cancer, Male; Bronchial Tumors; Burkitt Lymphoma; Carcinoid Tumor; Central Nervous System Atypical Teratoid/Rhabdoid Tumor; Central Nervous System Embryonal Tumors; Central Nervous System (CNS) Lymphoma, Primary Cervical Cancer; Cervical Cancer; Childhood Cancers; Chordoma; Chronic Lymphocytic Leukemia; Chronic Myelogenous Leukemia; Chronic Myeloproliferative Disorders; Colon Cancer; Colorectal Cancer;

Craniopharyngioma; Cutaneous T-Cell Lymphoma; Embryonal Tumors, Central Nervous System; Endometrial Cancer; Ependymoblastoma; Ependymoma; Esophageal Cancer; Esthesioneuroblastoma; Ewing Sarcoma Family of Tumors; Extracranial Germ Cell Tumor; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Hairy Cell Leukemia; Head and Neck Cancer; Heart Cancer; Hepatocellular (Liver) Cancer, Adult (Primary); Hepatocellular (Liver) Cancer; Histiocytosis, Langerhans Cell; Hodgkin Lymphoma, Adult; Hodgkin Lymphoma, Childhood; Hypopharyngeal Cancer; Intraocular Melanoma; Islet Cell Tumors (Endocrine Pancreas); Kaposi Sarcoma; Kidney (Renal Cell) Cancer; Kidney Cancer; Langerhans Cell Histiocytosis; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin, Adult; Lymphoma, Hodgkin, Childhood; Lymphoma, Non-Hodgkin, Adult; Lymphoma, Non-Hodgkin, Childhood; Lymphoma, Primary Central Nervous System (CNS); Macroglobulinemia, Waldenström; Malignant Fibrous Histiocytoma of Bone and Osteosarcoma; Medulloblastoma; Medulloepithelioma; Melanoma; Melanoma, Intraocular (Eye); Merkel Cell Carcinoma; Mesothelioma, Adult Malignant; Mesothelioma; Metastatic Squamous Neck Cancer with Occult Primary; Mouth Cancer; Multiple Endocrine Neoplasia Syndrome; Multiple Myeloma/Plasma Cell Neoplasm; Mycosis Fungoides; Myelodysplastic Syndromes; Myelodysplastic/Myeloproliferative Neoplasms; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Hodgkin Lymphoma, Adult; Non-Hodgkin Lymphoma, Childhood; Non-Small Cell Lung Cancer; Oral Cancer; Oral Cavity Cancer, Lip and; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Paranasal Sinus and Nasal Cavity Cancer; Parathyroid Cancer; Penile Cancer; Pharyngeal Cancer; Pineal Parenchymal Tumors of Intermediate Differentiation; Pituitary Tumor; Plasma Cell Neoplasm/Multiple Myeloma; Pleuropulmonary Blastoma; Pregnancy and Breast Cancer; Primary Central Nervous System (CNS) Lymphoma; Prostate Cancer; Rectal Cancer; Renal Cell (Kidney) Cancer; Renal Pelvis and Ureter, Transitional Cell Cancer; Respiratory Tract Cancer with Chromosome 15 Changes; Retinoblastoma; Rhabdomyosarcoma; Salivary Gland Cancer; Salivary Gland Cancer; Sarcoma, Ewing Sarcoma Family of Tumors; Sarcoma, Kaposi; Sarcoma, Soft Tissue, Adult; Sarcoma, Soft Tissue, Childhood; Sarcoma, Uterine; Sezary Syndrome; Skin Cancer (Nonmelanoma); Skin Cancer; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Cell Carcinoma; Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Unknown Primary Site, Carcinoma of; Ureter and Renal Pelvis, Transitional Cell Cancer; Urethral Cancer; Uterine Cancer, Endometrial; Uterine Sarcoma; Uveal melanoma; Vaginal Cancer; Vulvar Cancer; Waldenström Macroglobulinemia; or Wilms Tumor.

Administration Schedules

In certain embodiments, the methods, cells, culture medium, extracellular vesicles, and secreted factors of this disclosure are for administration to a subject in need of treatment for a cancer, autoimmune disorder, or inflammatory disorder. In certain embodiments, the methods, cells, and induction media of this disclosure encompass different routes of administration. In certain embodiments, the routes of administration are subcutaneous, intraparietal, intramuscular, intravenous, intratumor, intraocular, intraretinal, intravitreal, or intracranial. In a certain embodiment, the cells can be administered directly to tumor site or site of inflammation.

In certain embodiments, the methods, cells, culture media, extracellular vesicles, and secreted factors of this disclosure are for administration to a subject in need of treatment for a cancer, autoimmune disorder, or immune mediated inflammatory disease. In certain embodiments, the methods, cells, and induction medium of this disclosure encompass different dosage frequencies. In certain embodiments, cells and methods of this disclosure are administered once a day, once a week, once a month, or once a year. In certain embodiments, cells and methods of this disclosure are administered twice a day, twice a week, twice a month, or twice a year. In certain embodiments, cells and methods of this disclosure are administered thrice a day, thrice a week, thrice a month, or thrice a year. In certain embodiments, cells and methods of this disclosure are for administration four times a day, four times a week, four times a month, or four times a year. In certain embodiments, a primary treatment is followed by a maintenance dose 1, 2, 3, 4, 5, 6, 7, 8, 9, 10, 11, or 12 times a year. In certain embodiments, the maintenance dose is continued for at least 1, 2, 3, 4, 5, 6, 7, 8, 9, 10, or more years. In certain embodiments, at least $1 \times 10^6$ cells are administered per dose. In certain embodiments, at least $2 \times 10^6$ cells are administered per dose. In certain embodiments, at least $3 \times 10^6$ cells are administered per dose. In certain embodiments, at least $4 \times 10^6$ cells are administered per dose. In certain embodiments, at least $5 \times 10^6$ cells are administered per dose. In certain embodiments, at least $6 \times 10^6$ cells are administered per dose. In certain embodiments, at least $7 \times 10^6$ cells are administered per dose. In certain embodiments, at least $8 \times 10^6$ cells are administered per dose. In certain embodiments, at least $9 \times 10^6$ cells are administered per dose. In certain embodiments, at least $1 \times 10^7$ cells are administered per dose. In certain embodiments, at least $2 \times 10^7$ cells are administered per dose. In certain embodiments, at least $3 \times 10^7$ cells are administered per dose. In certain embodiments, at least $4 \times 10^7$ cells are administered per dose. In certain embodiments, at least $5 \times 10^7$ cells are administered per dose. In certain embodiments, at least $6 \times 10^7$ cells are administered per dose. In certain embodiments, at least $7 \times 10^7$ cells are administered per dose. In certain embodiments, at least $8 \times 10^7$ cells are administered per dose. In certain embodiments, at least $9 \times 10^7$ cells are administered per dose. In certain embodiments, at least $1 \times 10^8$ cells are administered per dose. In certain embodiments, at least $2 \times 10^8$ cells are administered per dose. In certain embodiments, at least $3 \times 10^8$ cells are administered per dose. In certain embodiments, at least $4 \times 10^8$ cells are administered per dose. In certain embodiments, at least $5 \times 10^8$ cells are administered per dose. In certain embodiments, at least $6 \times 10^8$ cells are administered per dose. In certain embodiments, at least $7 \times 10^8$ cells are administered per dose. In certain embodiments, at least $8 \times 10^8$ cells are administered per dose. In certain embodiments, at least $9 \times 10^8$ cells are administered per dose. In certain embodiments, at least $1 \times 10^9$ cells are administered per dose. In certain embodiments, at least $2 \times 10^9$ cells are administered per dose. In certain embodiments, at least $3 \times 10^9$ cells are administered per dose.

Pharmaceutically Acceptable Excipients, Diluents, and Carriers

The cells, media, and extracellular vesicles of the current disclosure can be combined with a pharmaceutically acceptable excipient, diluent, or carrier in order to improve and enhance administration, stability, uniformity, bioavailability, or any combination thereof. In certain embodiments, the extracellular vesicles or cells of the current disclosure are administered suspended in a sterile solution. In certain embodiments, the solution comprises 0.9% NaCl. In certain embodiments, the solution further comprises one or more of: buffers, for example, acetate, citrate, histidine, succinate, phosphate, bicarbonate, or hydroxymethylaminomethane (Tris); surfactants, for example, polysorbate 80 (Tween 80), polysorbate 20 (Tween 20), or poloxamer 188; polyol/disaccharide/polysaccharides, for example, glucose, dextrose, mannose, mannitol, sorbitol, sucrose, trehalose, or dextran 40; amino acids, for example, glycine or arginine; antioxidants, for example, ascorbic acid or methionine; and chelating agents, for example, EDTA or EGTA. In certain embodiments, the extracellular vesicles of the current disclosure are shipped/stored lyophilized and reconstituted before administration. In certain embodiments, lyophilized extracellular vesicle formulations comprise a bulking agent such as mannitol, sorbitol, sucrose, trehalose, and dextran 40.

Examples

The following examples are meant to be illustrative and do not serve to limit the invention described herein.

Figure 3A:
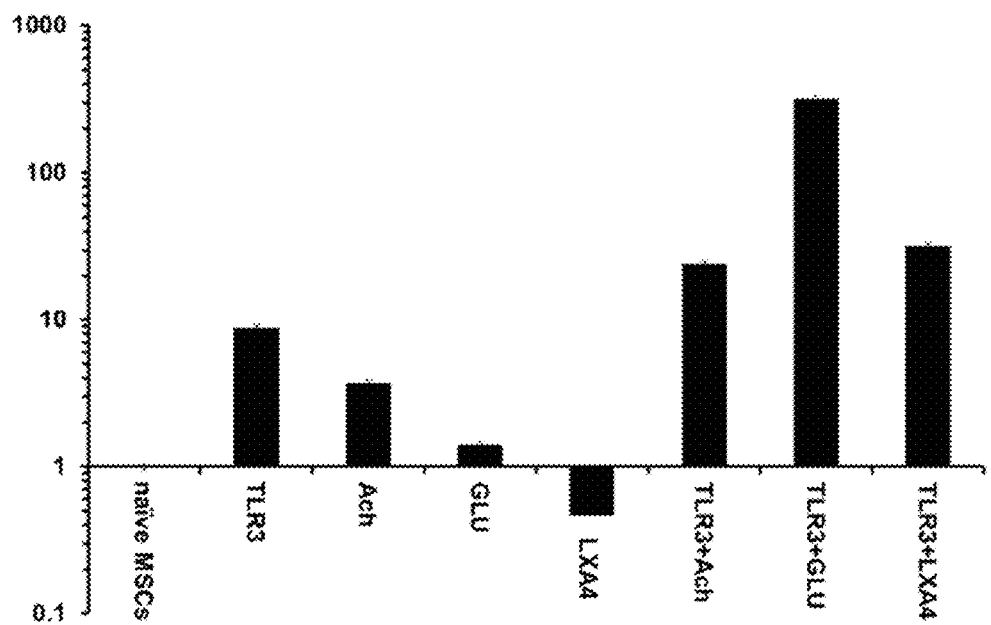
FIGS. 3A and B illustrates induction of CXCL9 mRNA expression by mesenchymal stem cells in response to stimulation with inducing agents in combination with TLR3.
Figure 3B:
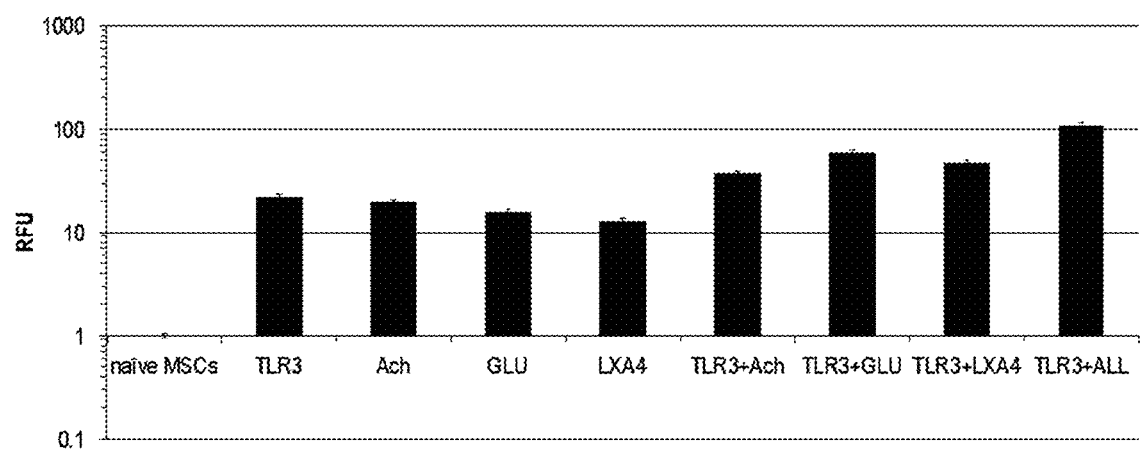

Example-1 Enhancement of Mesenchymal Stem Cell Priming by Combination of Toll-Like Receptor and Certain Inducing Agents Referring to FIG. 3A and FIG. 3B, Type 2 mesenchymal stem cell priming by TLR3 is further enhanced with Acetylcholine (ACH), Glutamate (GLU), and Lipoxin A4 (LAX4). Human bone marrow derived mesenchymal stem cells were induced into type 2 mesenchymal cells using poly(I:C) and 0.5 ng/mL of human recombinant erythropoietin. Total RNA was isolated, purified, and reverse transcribed to cDNA. Quantitative real-time PCR was carried out using SYBR Green Master Mix. Data were analyzed using the quantitative comparative CT method, normalizing target gene expression to the 18S rRNA housekeeping gene, and shown as fold increase over the untreated control. CXCL9 gene expression was significantly increased following induction. Error bars represent +/−the standard error of the mean (SEM). As shown in two independent experiments in FIGS. 3A and 3B, stimulation of mesenchymal stem cells with a combination of TLR3 and either ACH (approx. 24-fold FIG. 3A; approx. 37-fold FIG. 3B), GLU (approx. 317.4-fold FIG. 3A; approx. 59-fold FIG. 3B), LAX4 (approx. 32-fold FIG. 3A; approx. 47-fold FIG. 3B), or all three combined (approx. 108-fold FIG. 3B) resulted in greater expression of CXCL9 than any one alone TLR3 (approx. 8.8-fold FIG. 3A; approx. 22-fold FIG. 3B), ACH (approx. 3.7-fold FIG. 3A; approx. 20-fold FIG. 3B), GLU (approx. 1.4-fold FIG. 3A; approx. 16-fold FIG. 3B), or LAX4 (approx. −2-fold FIG. 3A; approx. 13-fold FIG. 3B).

Figure 4A:
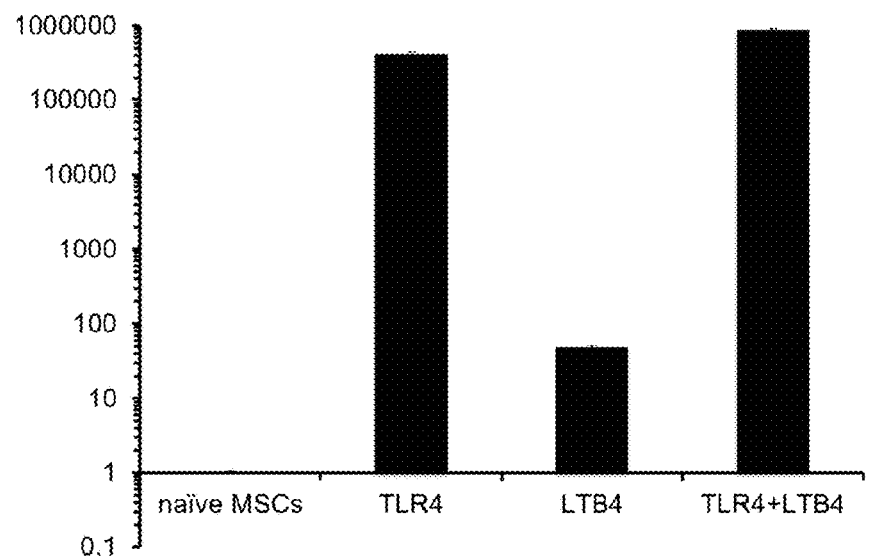
FIGS. 4A and B illustrates induction of TNFSF10 (also known as TRAIL) mRNA expression by mesenchymal stem cells in response to stimulation with inducing agents in combination with TLR4.
Figure 4B:
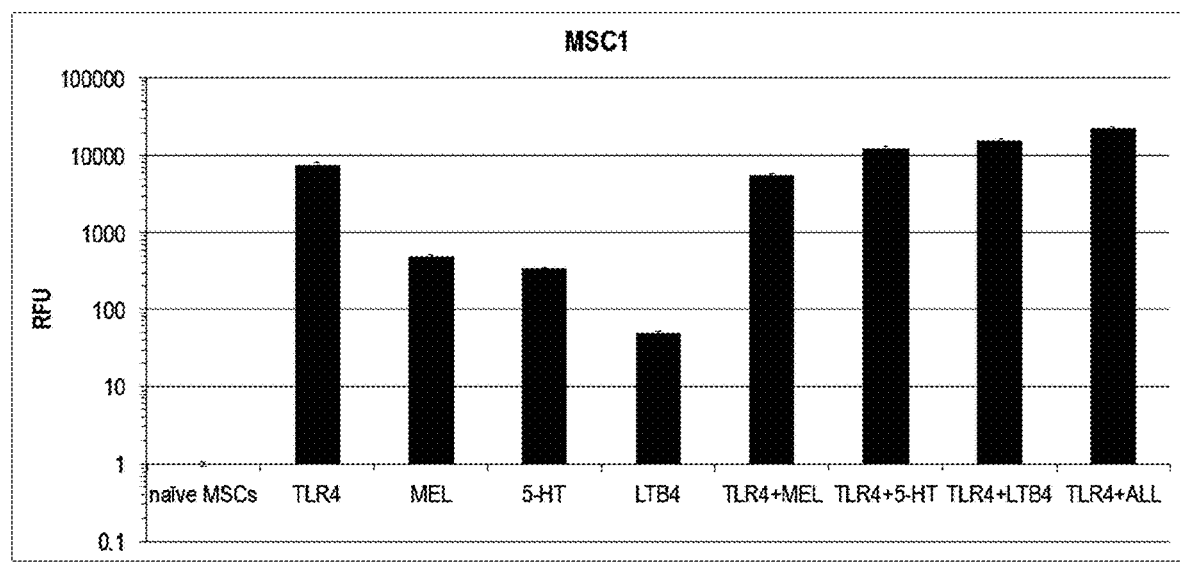

Referring to FIG. 4A and FIG. 4B, Type 1 mesenchymal stem cell priming by TLR4 is further enhanced with leukotriene B4 (LTB4), serotonin (5-HT), melatonin (MEL). Human bone marrow derived mesenchymal stem cells were induced into type 1 mesenchymal stem cells using lipopolysaccharide (LPS) and 0.5 ng/mL of human recombinant erythropoietin. Total RNA was isolated, purified, and reverse transcribed to cDNA. Quantitative real-time PCR was carried out using SYBR Green Master Mix. Data were analyzed using the quantitative comparative CT method, normalizing target gene expression to the 18S rRNA housekeeping gene, and shown as fold increase over the untreated control. TNFSF10 (also known as TRAIL) gene expression was significantly increased following induction. Error bars represent +/−the standard error of the mean (SEM). As shown in two independent experiments in FIGS. 4A and 4B stimulation of mesenchymal stem cells with a combination of TLR4 and either LTB4 (approx. 875,457-fold FIG. 4A; approx. 15,437-fold FIG. 4B), 5-HT (approx. 12,323-fold FIG. 4B), MEL (approx. 5,555-fold FIG. 4B), or all three combined (approx. 22,238-fold FIG. 4B), resulted in greater expression of TNFSF10 than any one alone. TLR4 (approx. 425,854-fold FIG. 4A; approx. 7,567-fold FIG. 4B), LTB4 (approx. 49-fold FIG. 4A; approx. 49-fold FIG. 4B), 5-HT (approx. 333-fold FIG. 4B), or MEL (approx. 489-fold FIG. 4B).

Example 2—Analysis of Factors Secreted by Primed Mesenchymal Stem Cells

The secretion of broad range bioactive molecules (i.e., secretome) is an important mechanism by which MSCs achieve their therapeutic effect and that likely most affect the targeted diseased tissue. We include exosomes [also referred to as extracellular vesicles; EVs or multi-vesicular bodies; MEBs] as a known contributor to these bioactive factors. Exosomes are secretory vesicles that can affect neighboring cells. We include mitogens, Extracellular Matrix (ECM) proteins, angiogens, exosomes, and inflammatory/immune modulating bioactive factors as molecules potentially contributed by MSCs.

Naïve MSC, MSC1, and MSC2 secretomes/exosomes were tested by Bio-Plex Bioactive Factor Assays following the manufacturer's instructions (Human Group I & II; Bio-Rad, Hercules, CA), miRNA analyses by Sistemic Inc (UK), Phalanx Biotech group (CA), next generation protein sequencing by LC-MS/MS System Biosciences (SBI, CA), and subsequently validated by Western blot analysis, ELISA, flow cytometry, and RT-qPCR.

Conditioned medium from naïve MSCs, MSC1, and MSC2 was collected and clarified by centrifugation prior to bioactive factor analyses. MSC1 were stimulated by treatment of human bone marrow derived mesenchymal stem cells using 10 ng/mL of LPS for 48 hours. MSC2 were stimulated by treatment of human bone marrow derived mesenchymal stem cells using 1 ug/mL of poly(I:C) for 48 hours. All levels were normalized by total protein concentration in samples and further by the untreated naïve MSC levels. Levels greater than 4-fold were considered statistically significant. Data are representative of greater than 3 independent experiments and further validated by ELISA or Western Blot analysis. Results are shown below in Table 1.

TABLE 1

| Elevated Factors | |
|---|---|
| MSC1 | MSC2 |
| IL3 | IL4 |
| IL17 | IL13 |
| IL6 | IL10 |
| IL8 | TGF beta |
| Interferon beta | PGE2 |
| LIF | IDO |
| GM-CSF | CXCL9 |
| MIG | CCL5 |
| MCP1 | CXCL10 |
| TRAIL | |

Abbreviations: CCL, C-C motif chemokine ligand; CXC, C-X-C motif chemokine; CXCL, CXC-ligand; GM-CSF, granulocyte-macrophage-colony stimulating factor; IDO, indoleamine 2,3-dioxygenase; IL, interleukin; IP-10, interferon-gamma-inducible protein 10 (CXCL10); LIF, leukemia inhibitory factor; MCP-1, monocyte chemoattractant protein-1 (CCL2); MIG, Monokine induced by gamma interferon; PGE2, prostaglandin-E2; RANTES, regulated upon activation normal T cell expressed and secreted (CCL5); TGF beta, transforming growth factor beta; TRAIL, TNF-related apoptosis-inducing ligand (TRAIL).

The results show a distinct non overlapping set of secreted factors that are secreted by MSC1 and MSC2. In general, pro-inflammatory factors are secreted by MSC1 and anti-inflammatory factors are secreted by MSC2.

Example 3—Analysis of Protein Content of Extracellular Vesicles Secreted by Primed Mesenchymal Stem Cells Extracellular vesicles from naïve MSCs, MSC1, and MSC2 were isolated and analyzed by liquid chromatography [LC]-mass spectroscopy [MS]/MS using the ExoQuick-TC kit (System Biosciences, Inc). Briefly, conditioned medium from naïve, MSC1, and MSC2 were collected after 48 hrs of incubation in serum/animal-free medium and clarified by centrifugation. MSC1 were stimulated by treatment of human bone marrow-derived mesenchymal stem cells using 10 ng/mL of LPS and 5 ng/mL of human recombinant erythropoietin for 48 hours prior to assay. MSC2 were stimulated by treatment of human bone marrow-derived mesenchymal stem cells using 1 ug/mL of poly(I:C) and 5 ng/mL of human recombinant erythropoietin for 48 hours prior to assay. Extracellular vesicles pellets were lysed in 200 µL modified RIPA buffer (2.0% SDS, 150 mM NaCl, 50 mM Tris, pH 8.5, 1× Complete Protease inhibitor (Roche)) at 100° C. for 15 minutes. The lysate was clarified by centrifugation and the protein concentration determined by Qubit fluorometry (Invitrogen). 10 µg of extracted protein was processed by SDS-PAGE using 10% Bis Tris NuPage mini-gel (Invitrogen) in the MES buffer system. The migration window (2 cm lane) was excised and in-gel digestion performed using a ProGest robot (DigiLab). Half of each digested sample was analyzed by nano LC-MS/MS with a Waters NanoAcquity HPLC system interfaced to a ThermoFisher Q Exactive. Peptides were loaded on a trapping column and eluted over a 75 µm analytical column at 350 nL/min using a 2 hr reverse phase gradient; both columns were packed with Luna C18 resin (Phenomenex). The fifteen most abundant ions were selected for MS/MS. The results are shown below in Table 2.

TABLE 2

| Protein composition of MSC1 and MSC2 extracellular vesicles | | | |
|---|---|---|---|
| Identified Proteins | Accession Number | MSC1/naïve MSC | MSC2/naïve MSC |
| Glyceraldehyde-3-phosphate dehydrogenase OS = Homo sapiens GN = GAPDH PE = 1 SV = 3 | sp\|P04406\|G3P_HUMAN | 19.22658021 | 0 |
| Junction plakoglobin OS = Homo sapiens GN = JUP PE = 1 SV = 3 | sp\|P14923\|PLAK_HUMAN | 18.28869825 | 1.833504151 |
| Pyruvate kinase PKM OS = Homo sapiens GN = PKM PE = 1 SV = 4 | sp\|P14618\|KPYM_HUMAN | 11.93373944 | 3.888293286 |
| Desmoplakin OS = Homo sapiens GN = DSP PE = 1 SV = 3 | sp\|P15924\|DESP_HUMAN | 10.42404951 | 0 |
| Moesin OS = Homo sapiens GN = MSN PE = 1 SV = 3 | sp\|P26038\|MOES_HUMAN | 6.785851838 | 0 |
| Vimentin OS = Homo sapiens GN = VIM PE = 1 SV = 4 | sp\|P08670\|VIME_HUMAN | 6.408860069 | 0 |
| Actin, cytoplasmic 1 OS = Homo sapiens GN = ACTB PE = 1 SV = 1 | sp\|P60709\|ACTB_HUMAN (+1) | 2.118092876 | 1.65629887 |
| Annexin A2 OS = Homo sapiens GN = ANXA2 PE = 1 SV = 2 | sp\|P07355\|ANXA2_HUMAN | 2.118092876 | 0 |
| Alpha-enolase OS = Homo sapiens GN = ENO1 PE = 1 SV = 2 | sp\|P06733\|ENOA_HUMAN | 1.694474301 | 0 |
| Collagen alpha-1(I) chain OS = Homo sapiens GN = COL1A1 PE = 1 SV = 5 | sp\|P02452\|CO1A1_HUMAN | 0.651720885 | *0.509630421* |
| Thrombospondin-1 OS = Homo sapiens GN = THBS1 PE = 1 SV = 2 | sp\|P07996\|TSP1_HUMAN | 0.553962752 | *0.339753614* |
| Collagen alpha-2(VI) chain OS = Homo sapiens GN = COL6A2 PE = 1 SV = 4 | sp\|P12110\|CO6A2_HUMAN | *0.494221671* | *0.368066415* |
| Decorin OS = Homo sapiens GN = DCN PE = 1 SV = 1 | sp\|P07585\|PGS2_HUMAN | *0.484135514* | *0.473228248* |
| Insulin-like growth factor-binding protein 7 OS = Homo sapiens GN = IGFBP7 PE = 1 SV = 1 | sp\|Q16270\|IBP7_HUMAN | *0.423618575* | *0.828149435* |
| Lysyl oxidase homolog 2 OS = Homo sapiens GN = LOXL2 PE = 1 SV = 1 | sp\|Q9Y4K0\|LOXL2_HUMAN | *0.423618575* | 0 |

TABLE 2-continued

Protein composition of MSC1 and MSC2 extracellular vesicles

| Identified Proteins | Accession Number | MSC1/naïve MSC | MSC2/naïve MSC |
|---|---|---|---|
| Biglycan OS = Homo sapiens GN = BGN PE = 1 SV = 2 | sp|P21810|PGS1_HUMAN | *0.376549845* | 0.981510441 |
| Collagen alpha-3(VI) chain OS = Homo sapiens GN = COL6A3 PE = 1 SV = 5 | sp|P12111|CO6A3_HUMAN | *0.325860442* | *0.169876807* |
| Myosin-1 OS = Homo sapiens GN = MYH1 PE = 1 SV = 3 | sp|P12882|MYH1_HUMAN | 0 | 7.079134862 |
| Myosin-2 OS = Homo sapiens GN = MYH2 PE = 1 SV = 1 | sp|Q9UKX2|MYH2_HUMAN | 0 | 9.438846483 |
| Myosin-7 OS = Homo sapiens GN = MYH7 PE = 1 SV = 5 | sp|P12883|MYH7_HUMAN | 0 | 5.730728222 |
| Sulfhydryl oxidase 1 OS = Homo sapiens GN = QSOX1 PE = 1 SV = 3 | sp|O00391|QSOX1_HUMAN | 0 | *0.441679699* |
| Tissue factor pathway inhibitor 2 OS = Homo sapiens GN = TFPI2 PE = 1 SV = 1 | sp|P48307|TFPI2_HUMAN | 0 | 2.208398493 |

Proteins significantly elevated compared to naïve unstimulated MSC are in bold; proteins significantly reduced compared to naïve unstimulated MSC are italicized.

Example 4—Analysis of miRNAs Expressed by Primed Mesenchymal Stem Cells

The microRNAs [miRNAs] were first described in nematodes about 20 years ago where they were important in determining cell fate. The presence of miRNAs in humans was first described a decade ago. miRNA profile studies have demonstrated that miRNAs are selectively expressed in different organs and at different developmental stages. The miRNA signatures for different tissue sources of MSCs have defined patterns of miRNAs involved in the maintenance of stem cell properties such as proliferation, self-renewal, and differentiation capacity. MSC1 and MSC2 miRNA profiles were analyzed from primed cells and compared to untreated naïve MSCs to reveal unique expression patterns. Data are representative of at least 3 independent experiments from more than 3 separate donors. Data are expressed as relative expression compared to naïve MSCs=1. For example, the elevated expression of the established pro-inflammatory miRNA155 in MSC1 is consistent with its predicted inflammatory phenotype.

MSC1 were stimulated by treatment of human bone marrow derived mesenchymal stem cells with 10 ng/mL of LPS and 5 ng/mL of human recombinant erythropoietin for 4 hours prior to assay. MSC2 were stimulated by treatment of human bone marrow derived mesenchymal stem cells with 1 ug/mL of poly(I:C) and 5 ng/mL of human recombinant erythropoietin for 4 hours prior to assay.

Figure 5A:
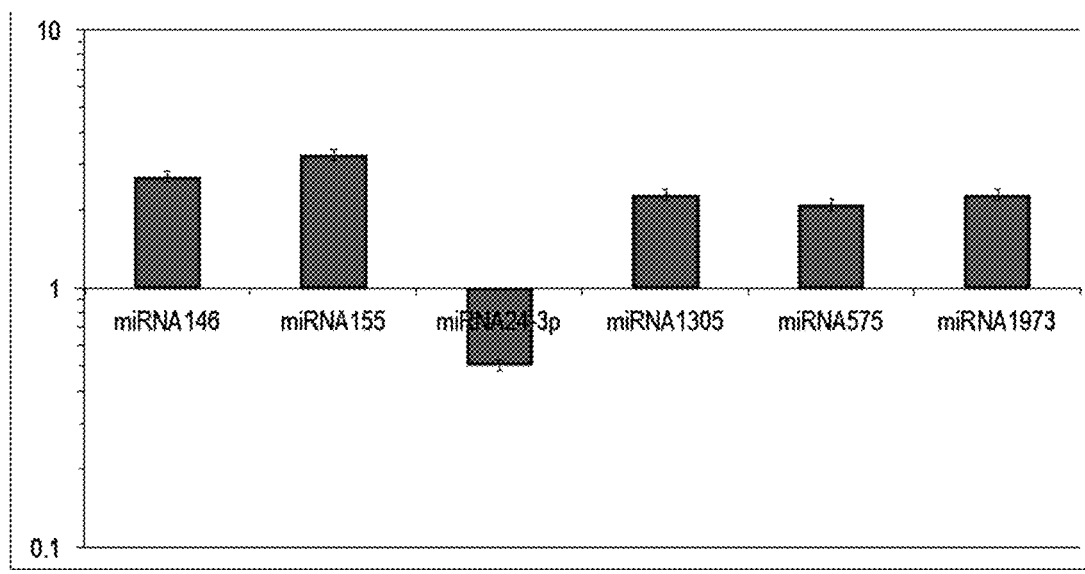
FIGS. 5A and B illustrates induction or reduction of miRNAs in mesenchymal stem cells that have been induced by TLR4 (FIG. 5A) or TLR3 (FIG. 5B).
Figure 5B:
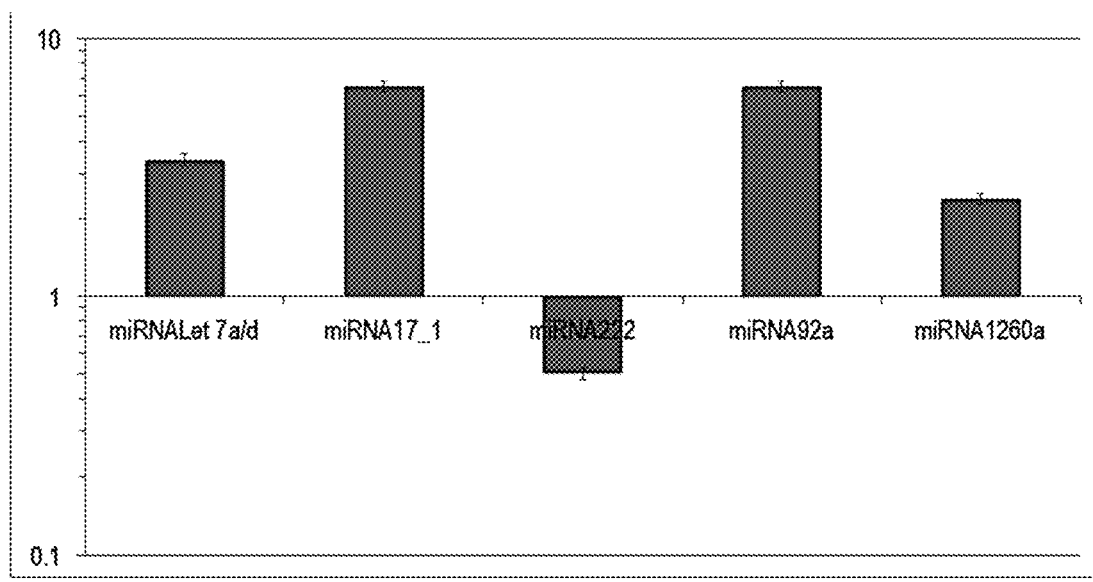

FIGS. 5A (MSC1) and B (MSC2) show results from these experiments. For MSC1-stimulated extracellular vesicles, levels of miR-146 (approx. 2.7-fold), miR-155 (approx. 3.3-fold), miR-1305(approx. 2.3-fold), miR-575 (approx 2.1-fold), and miR-1973(approx. 2.3-fold) were all induced greater than 2-fold compared to unstimulated MSC, while levels of miR-24-3p were reduced about 2-fold. For MSC2-stimulated extracellular vesicles, levels of miR-Let 7a/d (approx. 3.4-fold), miR-17_1 (approx. 6.5-fold), miR-92a (approx. 6.5-fold), and miR-1260a (approx. 2.4-fold) were all induced greater than 2-fold compared to unstimulated MSC, while levels of miR-222 were reduced about 2-fold.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

We claim:

1. A method for producing an immunologically polarized mesenchymal stem cell population from an unstimulated mesenchymal stem cell population comprising contacting the unstimulated mesenchymal stem cell population with a culture medium comprising:
   (a) a Toll-like receptor 3 (TLR3) ligand; and
   (b) an agent selected from the group consisting of one or more of acetylcholine, norepinephrine, epinephrine, serotonin, and melatonin;
   wherein expression of CXCL9 is induced in the immunologically polarized mesenchymal stem cell population.

2. The method of claim 1, wherein the TLR3 ligand comprises poly (I:C), poly (A:U), or a combination thereof.

3. The method of claim 1, wherein the culture medium further comprises erythropoietin.

4. The method of claim 1, wherein culture is conducted under hypoxic conditions.

5. The method of claim 4, wherein the hypoxic conditions comprise incubation in a hypoxic environment possessing less than 8% oxygen.

6. The method of claim 4, wherein the hypoxic conditions comprise incubation in a hypoxic environment possessing less than 4% oxygen.

7. The method of claim 4, wherein the hypoxic conditions comprise incubation in a hypoxic environment possessing between 0.5% to 3.0% oxygen.

8. The method of claim 1, wherein the agent is acetylcholine.

9. The method of claim 8, wherein the concentration of the acetylcholine is between 1 nanomolar (nM) to 100 micromolar (µM).

10. The method of claim 8, wherein the concentration of the acetylcholine is at least 1 nM.

11. The method of claim 8, wherein the concentration of the acetylcholine is at least 10 nM.

12. The method of claim 8, wherein the concentration of the acetylcholine is at least 100 nM.

13. The method of claim 8, wherein the concentration of the acetylcholine is at least 1 µM.

14. The method of claim 8, wherein the concentration of the acetylcholine is at least 10 µM.

15. The method of claim 1, wherein contacting the unstimulated mesenchymal stem cell population with the culture medium further comprises contacting the unstimulated mesenchymal stem cell population with the culture medium for less than 24 hours.

16. The method of claim 1, wherein contacting the unstimulated mesenchymal stem cell population with the culture medium further comprises contacting the unstimulated mesenchymal stem cell population with the culture medium for greater than 1 hour.

* * * * *